Figure 1A:
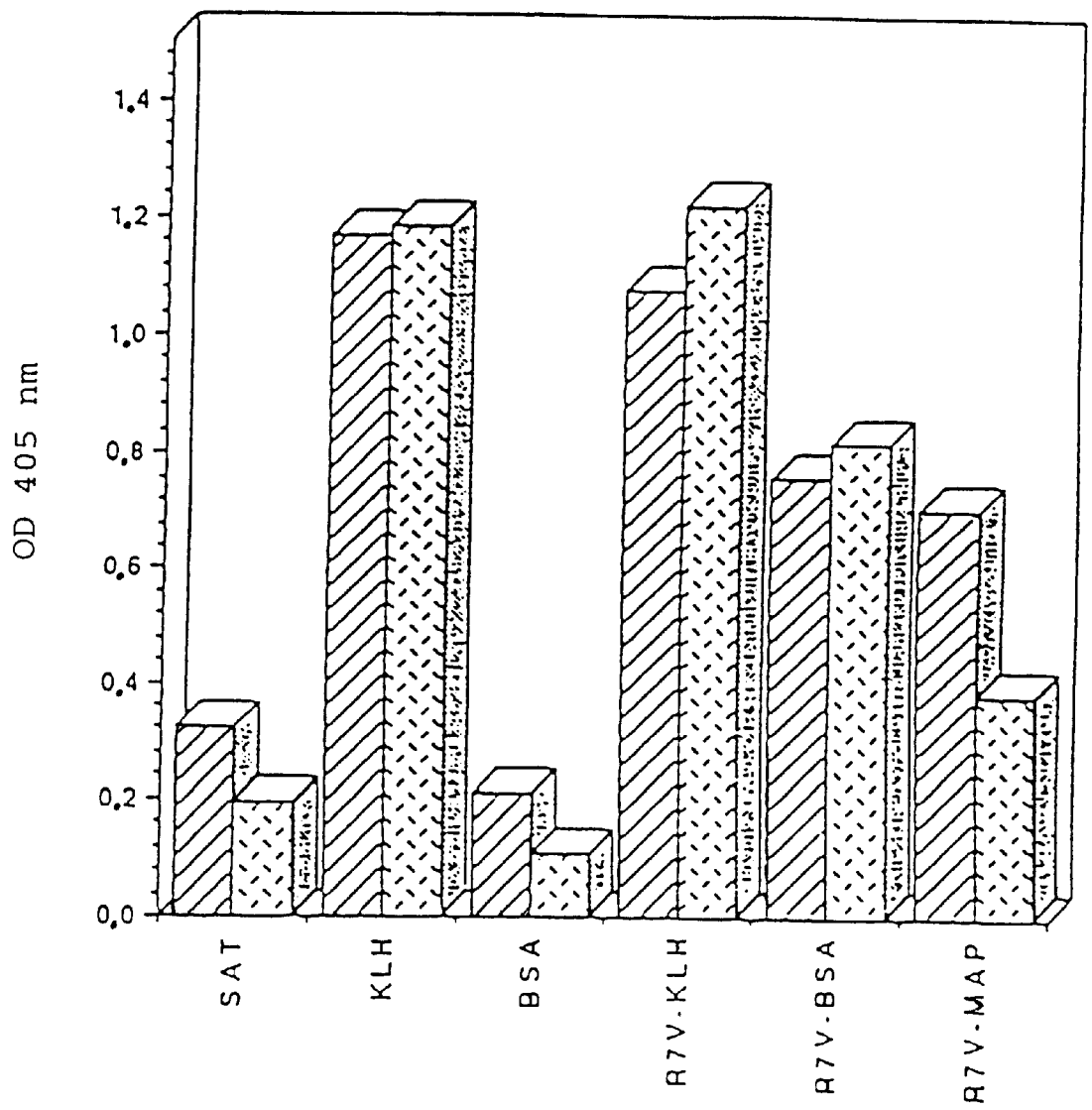

United States Patent [19]
Chermann et al.

[11] Patent Number: 6,113,902
[45] Date of Patent: Sep. 5, 2000

[54] IMMUNOGENIC COMPOSITIONS COMPRISING PEPTIDES FROM β-2-MICROGLOBULIN

[75] Inventors: Jean-Claude Chermann; Carole Le Contel; Pascale Galea, all of Marseille, France

[73] Assignee: Institut National de la Santa et de la Recherche Medicale (Inserm), Paris, France

[21] Appl. No.: 08/973,551

[22] PCT Filed: Jun. 28, 1996

[86] PCT No.: PCT/FR96/01006

§ 371 Date: Feb. 19, 1997

§ 102(e) Date: Feb. 19, 1997

[87] PCT Pub. No.: WO97/02344

PCT Pub. Date: Jan. 23, 1997

[30] Foreign Application Priority Data

Jun. 30, 1996 [FR] France ............................. 95 07914

[51] Int. Cl.[7] .................. A61K 39/00; A61K 39/38; A61K 39/21; A61K 39/12
[52] U.S. Cl. .................. 424/184.1; 424/280.1; 424/278.1; 424/279.1; 424/187.1; 424/204.1; 424/208.1; 530/324; 530/325; 530/326; 530/327; 530/328; 530/329; 530/330
[58] Field of Search .............. 424/280.1, 278.1, 424/279.1, 184.1, 187.1, 204.1, 208.1; 530/324, 325, 326, 327, 328, 329, 330

[56] References Cited

U.S. PATENT DOCUMENTS 5,733,550  3/1998  Rock ...................... 424/185.1

FOREIGN PATENT DOCUMENTS

| 0 229 723 | 7/1987 | European Pat. Off. ........ C07K 13/00 |
| 92/18630 | 10/1992 | WIPO . |
| 93/14126 | 7/1993 | WIPO . |
| 94/01130 | 1/1994 | WIPO . |
| 94/04171 | 3/1994 | WIPO . |
| 94/24290 | 10/1994 | WIPO . |

OTHER PUBLICATIONS

Haynes, et al. : Update on the issues of the HIV vaccine development: Ann. Med. : vol. 28: pp. 39–41, 1996.

Baltimore, et al.: Defeating AIDS: what will it take? : Scientific American: pp. 81–107, Jul. 1998.

Contel et al., "Identification Of The β2m Derived Epitope Responsible For Neutralization Of HIV Isolates", *Cellular Pharmacology*, vol. 3:68–73, (1996).

*Primary Examiner*—Jeffrey Stucker
*Assistant Examiner*—Brett Nelson
*Attorney, Agent, or Firm*—Foley & Lardner

[57] ABSTRACT

An immunogenic composition for treating and/or preventing infectious diseases where the infectious agent has at least one intracellular phase in the host during its multiplication cycle, is disclosed. The immunogenic composition comprises at least one cryptic epitope of a cellular element that is carried along by an intracellular infectious agent as it leaves the cell, and revealed by said infectious agent. A composition for treating and/or preventing HIV infections, antibodies to a peptide of interest, and a diagnostic method, are also disclosed.

12 Claims, 17 Drawing Sheets

IMMUNOGENIC COMPOSITIONS COMPRISING PEPTIDES FROM β-2-MICROGLOBULIN

This is a 371 of PCT/FR96/01006 filed Jun. 28, 1996.

The present invention relates to new types of vaccines and, in particular, to compositions intended for the treatment, prevention and diagnosis of HIV conditions.

More specifically, the present invention relates to peptides capable of producing an immune response capable of directly or indirectly neutralizing HIV viruses in mammals and in particular in man.

The importance of monoclonal antibodies directed against $β_2$-microglobulin (β2m) in the inhibition of HIV-1 replication has already been described, particularly in patent EP-B-0,470,989 as well as in various publications.

In particular, it has been possible to demonstrate that these antibodies act on two mechanisms, namely directly on the virus and on the cells associated with β2m.

The present invention constitutes developments of these preliminary elements and is based on the identification of peptide sequences obtained from β2m or having an equivalent structure which are capable of generating antibodies completely or partially neutralizing the HIV viruses.

Given the complexity of the mechanisms used, "neutralization of the HIV virus" will be understood to mean any mechanism having the effect in vivo of destroying and/or of preventing the propagation of viruses.

In vitro, these neutralizing antibodies can be used to neutralize any body fluid intended to be reinoculated or reintroduced into man, such as the sperm of a man seropositive for HIV for the insemination of a seronegative woman.

However, more generally, the present invention is based on a new vaccinal approach which can be used, in particular, for infectious agents of the parasite or virus type with a high mutating power. Indeed, in the context of traditional vaccination, it is sought to generate neutralizing antibodies directed against components of the infectious agent, but when the latter exhibits a high mutating power, such as HIV for example, this strategy gives, at best, only limited results for a particular isolate which will be very rapidly replaced by a mutant and resistant isolate.

The new vaccinal approach is based on a different concept and is applicable to a number of infectious agents which have an intracellular phase during their cycle.

Indeed, it is known for certain agents, or it is possible to demonstrate, especially in the case of HIV, which constitutes part of the present invention, that, during the multiplication of the infectious agents from the infected cells of the host, the extracellular infectious agents carry away components of determinants of the host cell.

One of the subjects of the present invention consists in taking as target, not the infectious agent itself, but the components of the determinant which it carries away with it and to provide for a vaccination directed against these cellular determinants which will remain constant, even if the agent itself has mutated.

This type of approach has, of course, an immediate limit, the antigen being bound to the host cells, it is only possible to carry out such a vaccination with a cryptic epitope of the cellular determinant which will be exposed only when it is carried away by the extracellular infectious agent, or an epitope which is nonimmunogenic in its natural presentation by the cell and which is modified when it is presented at the surface of the virion.

In the case of HIV for example, it has been possible to demonstrate that β2-microglobulin has several cryptic epitopes, which are exposed during the multiplication of the HIV virus and its passage outside the cell. There is not therefore, in the event of vaccination, on the one hand, an autoimmune reaction, and, on the other hand, the epitope being bound to the different HIV isolates which have been tested, the vaccination is effective, this being independent of the mutations of the virus itself.

This type of vaccination can be selected, in particular, for intracellular parasites and enveloped viruses such as CMV, HPV, HSV and HIV for example.

It should be clearly understood that while this type of vaccination cannot be used in all cases, it can constitute a very useful alternative for infectious agents which are resistant to more traditional approaches.

Accordingly, the present invention relates to a vaccine against an infectious agent, characterized in that it comprises at least one cryptic epitope of a cellular element carried away by an intracellular infectious agent during its passage outside the cell and which is exposed by the infectious agent.

Preferably, this infectious agent is a parasite or an envelope virus and the cryptic epitope is situated near the surface of the cell.

"Cryptic epitope" is intended to designate an epitope of a cellular determinant of the host which is hidden or modified and is therefore recognized as being foreign by the immune system and does not therefore produce an autoimmune reaction with destruction of the corresponding determinant and which can be used for vaccination.

The cryptic epitope should obviously be exposed, that is to say be accessible and recognized by the immune system when it is carried away by the infectious agent (in the event that it should remain cryptic, the vaccination would not be possible).

In the case of $β_2$-microglobulin, it has been possible to demonstrate the existence of this type of epitope which is in fact also found in a natural form during the elimination of β2-microglobulin by the urinary tract.

The present invention therefore relates to compositions intended for the treatment or prevention of HIV infections, characterized in that they comprise, as active ingredient, at least one peptide corresponding to sequences 1 to 22 or an equivalent sequence. "Equivalent sequence" is intended to designate a sequence which lifts the neutralization of the HIV virus by the monoclonal antibodies B1G6 or B262.2 in vitro.

These peptides constitute cryptic epitopes of 2-microglobulin as described above.

The peptides according to the present invention are the following (SEQ ID NOS 1–3, respectively)

01-P1 IQRTPKIQVYSRHPA (Ile-Gln-Arg-Thr-Pro-Lys-Ile-Gln-Val-Tyr-Ser-Arg-His-Pro-Ala)

02-P4 FHPSDIEVDLLKDGE (Phe-His-Pro-Ser-Asp-Ile-Glu-Val-Asp-Leu-Leu-Lys-Asp-Gly-Glu)

03-P9 ACRVNHVTLSQPKIV
  (Ala-Cys-Arg-Val-Asn-His-Val-Thr-Leu-Ser-Gln-Pro-Lys-Ile-Val)

It is also possible to use a smaller part (7 amino acids) of these 15 amino acids which lifts the neutralization of the virus by the monoclonal antibodies B1G6 or B2G2.2 (SEQ ID NOS 4–6, respectively):
04-R-7-V RTPKIQV (Arg-Thr-Pro-Lys-Ile-Gln-Val)
05-S-7-K SQPKIVK (Ser-Gln-Pro-Lys-Ile-Val-Lys)
06-F-7-E FHPSDIE (Phe-His-Pro-Ser-Asp-Ile-Glu)

A common structure PKI (3 amino acids) appears to be the unit which is responsible; hence the following amino acid modifications (SEQ ID NOS 7–12, respectively):
07-TLSRTPKIQV (Thr-Leu-Ser-Arg-Thr-Pro-Lys-Ile-Gln-Val) No. 185
08-IYLTQPKIKV (Ile-Tyr-Leu-Thr-Gln-Pro-Lys-Ile-Lys-Val) No. 186
09-IQRTPKIQVY (Ile-Gln-Arg-Thr-Pro-Lys-Ile-Gln-Val-Tyr) No. 187
10-TLSQPKIVKN (Thr-Leu-Ser-Gln-Pro-Lys-Ile-Val-Lys-Asn) No. 188
11-IQRTPQIVKW (Ile-Gln-Arg-Thr-Pro-Gln-Ile-Val-Lys-Trp) No. 189
12-IQRTPNIVKW (Ile-Gln-Arg-Thr-Pro-Asn-Ile-Val-Lys-Trp) No. 190

It is also possible to introduce a cysteine and a glycosylation site (SEQ ID NOS 13–16, respectively):
13-CYNPSDIE (Cys-Tyr-Asn-Pro-Ser-Asp-Ile-Glu)
14-YCNPEST (Tyr-Cys-Asn-Pro-Glu-Ser-Thr)
15-NFLNCYVS (Asn-Phe-Leu-Asn-Cys-Tyr-Val-Ser)
16-LNCYVSPSD (Leu-Asn-Cys-Tyr-Val-Ser-Pro-Ser-Asp)

Finally, it is possible to use the peptides using the different variations according to the species (mice, primates, rabbits, guinea pigs) (SEQ ID NOS 17–22, respectively):
17-KTPQIQV (Lys-Thr-Pro-Gln-Ile-Gln-Val)
18-FHPPQIE (Phe-His-Pro-Pro-Gln-Ile-Glu)
19-FHPPHIE (Phe-His-Pro-Pro-His-Ile-Glu)
20-AEPKTVY (Ala-Glu-Pro-Lys-Thr-Val-Tyr)
21-SQPKTVY (Ser-Gln-Pro-Lys-Thr-Val-Tyr)
22-ILSRTPKIQV (Ile-Leu-Ser-Arg-Thr-Pro-Lys-Ile-Gln-Val)

These peptides of SEQ ID NOS 1 to 22 contain only the preferential choice; it is possible, as has been indicated above, to find equivalent peptides.

Example 5 describes a method which makes it possible to identify the equivalent peptides.

These peptides are preferably bound to a carrier system; this may be either one or more protein fragments linked to the N- and/or C-terminal ends of said peptides in order to allow, in particular, an immune response; they will then be referred to as "conjugated proteins". Among the proteins which can be used, there may be mentioned in particular albumins, KLH (Keyhole Limpet Hemocyanin) MAP (Multiple Antigenic Peptide) or other proteins known for their immunogenicity. It is also possible to envisage proteins or protein fragments linked through nonpeptide bonds such as a disulfide bridge or bonds through a calcium ion.

During the study of the various peptides according to the invention, it emerged, although this is only a theory which cannot limit the present invention in any manner, that the PKI structure plays an essential role. Indeed, proline is an amino acid which imposes a conformation and which limits the possibility of a quaternary peptide configuration. Under these conditions, KI (Lys, Ile) is attached in a position which is exposed to reacting with an antibody.

Under these conditions, during the construction of the carrier proteins, it is advisable to provide preferably for a structure which leaves the PKI structure accessible.

Analysis of the structure of the regions selected for P1, P9 and P10 can be carried out by methods such as the selection using alanine to replace each amino acid separately, particularly in the RTPKIQV (SEQ ID NO:4) region, in order to determine the possible amino acids. It is also possible to use techniques using biotinilation of each peptide, followed by selction by EIA with the antibodies in order to determine the loss of attachment.

It is thus possible to envisage conjugating the epitopes in question with nonprotein components, for example polysaccharides and/or lipids, in order to constitute lipoproteins having enhanced vaccinating activities; here again, it is possible to envisage covalent bonds or otherwise.

These various types of compounds can be obtained either by chemical synthesis or by recombinant routes using techniques known in the field of production of recombinant proteins.

The flexibility of recombinant technologies makes it possible to produce proteins having a plurality of identical or different epitopes and capable of enhancing the activity of the final product. It is also possible to envisage the co-expression of various components entering into the compositions according to the invention.

According to one of the aspects of the invention, it will be possible for the peptide to be introduced into a known structural protein of HIV; in particular, constructs in which the peptide of interest is inserted into the hypervariable region of the V3 loop of gp120 can be used.

The V3 region of gp120 is the principal HIV-1 neutralization domain and one of the major determinants of viral tropism. Consequently, this type of mutant can be useful for studying the neutralization of HIV-1 linked to R7V and the modifications of its host spectrum. The high variability of the V3 region of gp120 among the isolates of HIV-1 is another reason for the preference for this region. It has been assumed that the replacement of the sequence of seven amino acids in the V3 region had greater chances of leading to a viable recombinant than a mutation in another, more conservative, region of the HIV-1 genome. The recombinant protein gp120/R7V can be expressed in parallel in a suitable system for expression of a protein in order to obtain a large quantity of immunogen R7V.

The use of carrier proteins is not essential; it is possible to provide optionally for other carrier systems. "Carrier system" is intended to designate any component which makes it possible to lead to a unit generating an immune response against the peptide in question, or which makes it possible to protect the peptide from elimination, particularly from a rapid proteolysis.

The compositions according to the invention may also comprise components which increase the immunogenicity of the peptides and/or proteins, particularly immunity adjuvants, specific or otherwise, such as Freund's adjuvant, polysaccharides or equivalent compounds.

These are methods which are known in the vaccination field.

The compositions according to the invention can be used in any form compatible with the route of administration chosen, in particular the injectable route. However, it will be possible for the compositions according to the present invention to be used by other routes, particularly per Os or by the aerosol route, to induce protection of the mucous membranes.

The present invention also relates to compositions intended to be administered in order to express in situ the peptides and/or proteins described above.

In particular, the present invention relates to DNA expression cassettes which make it possible to express at least one cryptic epitope as defined above, and in particular the peptide having sequence 1 to 22 and/or the proteins having these peptides or proteins capable of coupling with the peptide in question as defined above or having equivalent sequences.

"Equivalent sequence" is intended to designate a sequence encoding an equivalent peptide as has been described above.

These DNA expression cassettes can, of course, be used either directly for expression in situ, or can be used to produce a peptide or protein which can be used as has been described above.

Vaccination systems using DNA sequences are known and are already widely described in the literature.

They are essentially systems allowing the expression of the antigenic protein in man, or the expression of the antigenic protein in a cell, which is then used for the vaccination; when the transformed cell is a host cell treated outside, the treatment is said to be ex vivo.

The expression systems may be highly varied; they may be in particular "naked DNA" type systems as are described in particular in the patents and patent applications of the company VICAL, WO 90/11092. In this case, the DNA encoding the peptide or protein comprising the peptide is injected as it is; this injection leads, in a number of cases, to the expression of the encoded protein.

The information contained in these documents is explicitly included in the present description by reference.

It will also be possible to use "naked DNA" systems, but comprising their own expression system, particularly in order to enhance the expression.

It will also be possible to use systems promoting the expression, either by integration, or by autonomous replication, particularly of systems of the plasmid or viral type.

Among the systems for expression of a peptide sequence which may be mentioned, there should be mentioned the systems using poxviruses, adenoviruses, retroviruses and herpes-type viruses or other more recent systems such as polioviruses.

Among the vectors, vectors generating a humoral response and for the mucous membranes will preferably be used.

Other viruses can be used in order to obtain vaccines in particular:

the adenoviruses as is described in N. R. Rabinovich et al., Science, 1994, 265, 1401–1404 and references cited;
the rotaviruses as is described by Sue E. Crowford, in Journal of Virology, Sept. 1994, p. 5945–5952;
the poxviruses, particularly the vaccinia virus, also animal poxviruses such as the canari pox as is described in the work by Paoletti and Moss;
influenza virus as described in N. R. Rabinovich et al. (1994).

The technology which makes it possible to use the polioviruses as vaccination vector for various antigens is described particularly in Raul Andino et al., Science, 265, 1448–51.

This type of construct, which can be used in the context of the present invention, makes it possible to obtain vaccines which can be used by the oral route; to do this, the sequence encoding the peptide(s), optionally the carrier proteins, is cloned into a poliovirus, for example the attenuated Sabin virus; it is also possible to use a cocktail of viruses encoding various epitopes.

The use of plasmids or of viruses for the expression of proteins in the cells of a host, particularly a human host, is known and will not be explained in detail. The specific constructs obviously depend on the host, the epitope and the vector selected.

It is also possible to use cellular vaccines, that is to say, for example as is proposed in the context of gene therapy, to collect cells from the patient, to transform them with vectors as described above and then to reimplant them in order to express the proteins in situ.

However, in the case of a vaccination, this method is not very convenient. It will be preferable to use cells which can be obtained in a large number, bacterial or yeast cells for example, which express the protein in question, for example at the surface, which, in some cases, increases the immunogenicity of the protein.

It is possible, for example, to use vaccines comprising, as expression system, Salmonella as is described in T. R. Fouts et al., Vaccine (1995) 13 in press; Tacket C. O. et al., Infect. Immun. (1992) 60, 536–541 and Hone et al., J. Chim. Invest. (1992) 90, 412–420 (for its evaluation in man as vaccinal support).

This type of vaccine involves the use of cells, particularly bacterial cells, producing the peptides according to the invention or certain strains of other vaccination vectors and described in Chad P Muller, Immunology Today. vol. 15 No. 20. 1994, p. 458–459.

The cells producing the peptides or proteins according to the invention can be used as they are, in particular when the proteins are expressed at the surface of the cells and when the cells are nontoxic and non-pathogenic (attenuated or killed strain), but can also be used to produce the peptides and/or proteins which will be used after purification.

Thus, it may be advantageous to obtain bacterial cells, but also yeasts or higher cells, animal, plant or insect cells in particular.

In the case of the present invention, it is possible to provide for the use of vaccines of plant origin using the technologies described particularly in C. J. Arntzel et al. in Vaccine 94.

The technologies allowing the expression of the peptides or proteins by cellular systems are known, as well as the purification techniques.

As has already been mentioned, it is possible to use the compositions according to the invention with adjuvants enhancing the activity of the DNA sequences, particularly components constituting complexes with the DNA, such as cationic lipids or structures of the liposome or microparticle type.

The invention also relates to compositions containing antibodies against the peptides according to the invention or compositions containing sequences encoding antibodies directed against the peptides according to the invention.

Of course, the use of compositions based on antibodies requires that the latter are compatible with administration to a human being; they may be in particular antibodies humanized by known techniques or directly expressed in situ from the DNA sequence.

The present invention also relates to the use of the antibodies raised against the peptides of the invention and capable of neutralizing the HIV virus, in particular the present invention relates to anti-sera comprising this type of antibody or the antibodies obtained, for example by immunopurification, from the said sera.

The present invention also relates to a method of diagnosis, characterized in that the presence of an antibody directed against one of the epitopes according to the invention is detected in the serum of a patient.

This method can be carried out by any known method for identifying antibodies, particularly the ELISA and RIA methods and all the methods derived therefrom.

All these methods are preferably based on the attachment of the antibodies in question onto the antigenic peptides described above, followed by the visualization of this attachment. This diagnosis is of considerable interest; indeed, examples show that seropositive individuals in the case of HIV who have antibodies according to the invention do not, in a very large number of cases, progress, that is to say that they do not develop AIDS. In this case, the prognosis is very favorable and it is possible to avoid expensive treatments. This is particularly true in the case of pregnancy where the presence of these antibodies in the mother (HIV+) would seem to lead to noninfection of the newborn.

The production of the compositions according to the present invention can be carried out by techniques which are known, synthesis of protein by the chemical route, synthesis of DNA by the chemical route or multiplication by PCR-type amplification. For the proteins, these can also be obtained by the recombinant route using appropriate syntheses.

The examples below will make it possible to demonstrate other characteristics and advantages of the present invention.

Figure 1B:
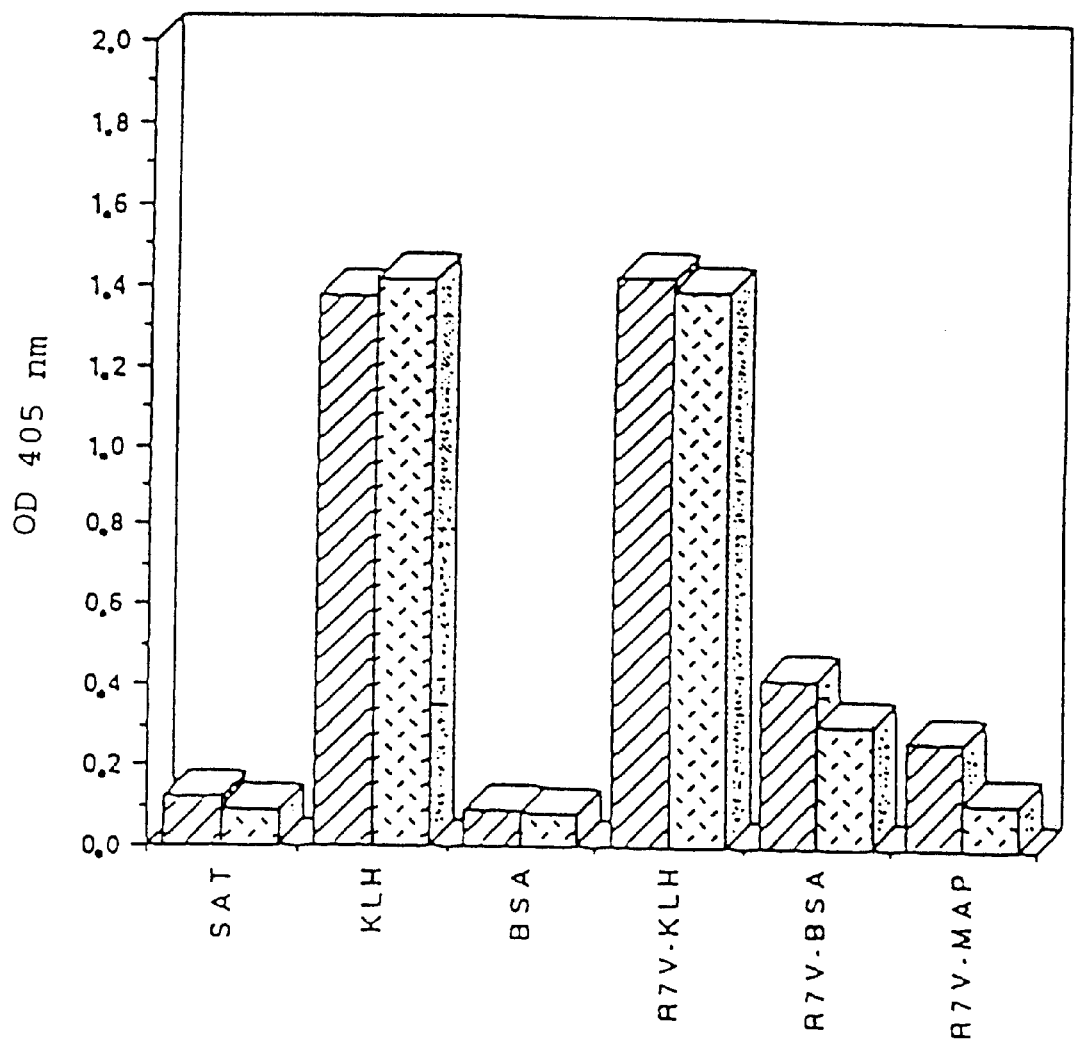
Figure 2:
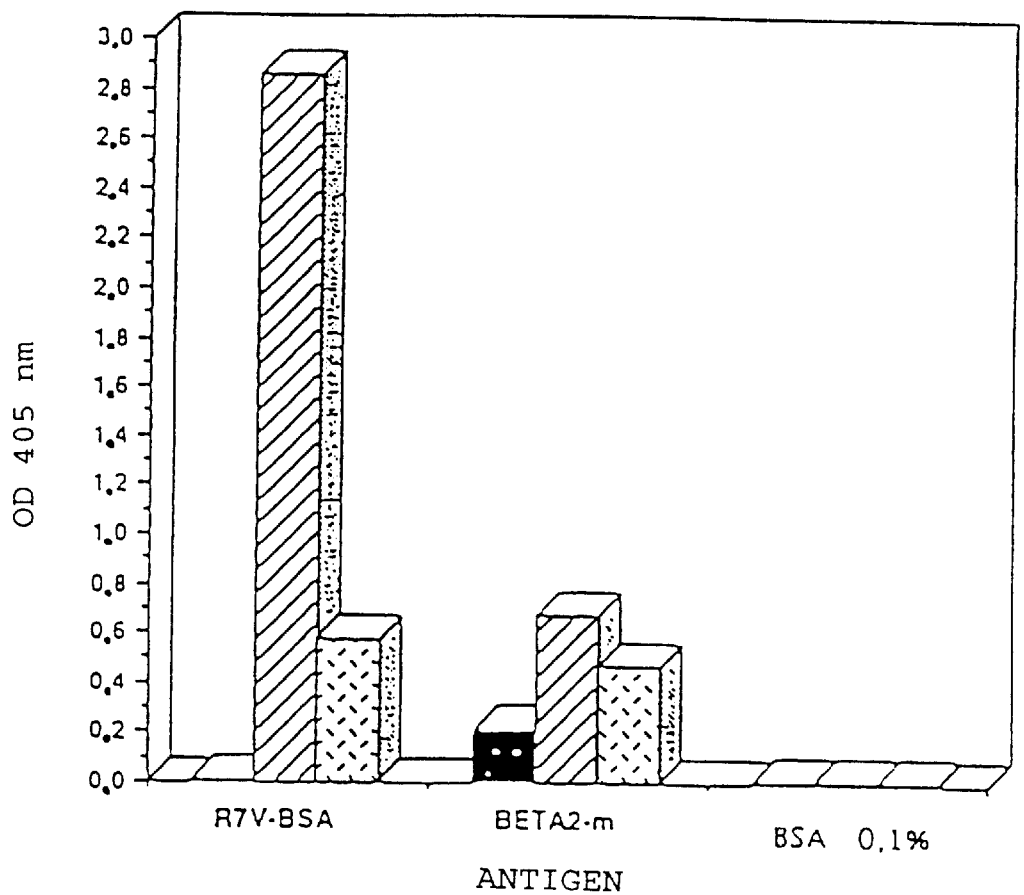
Figure 3A:
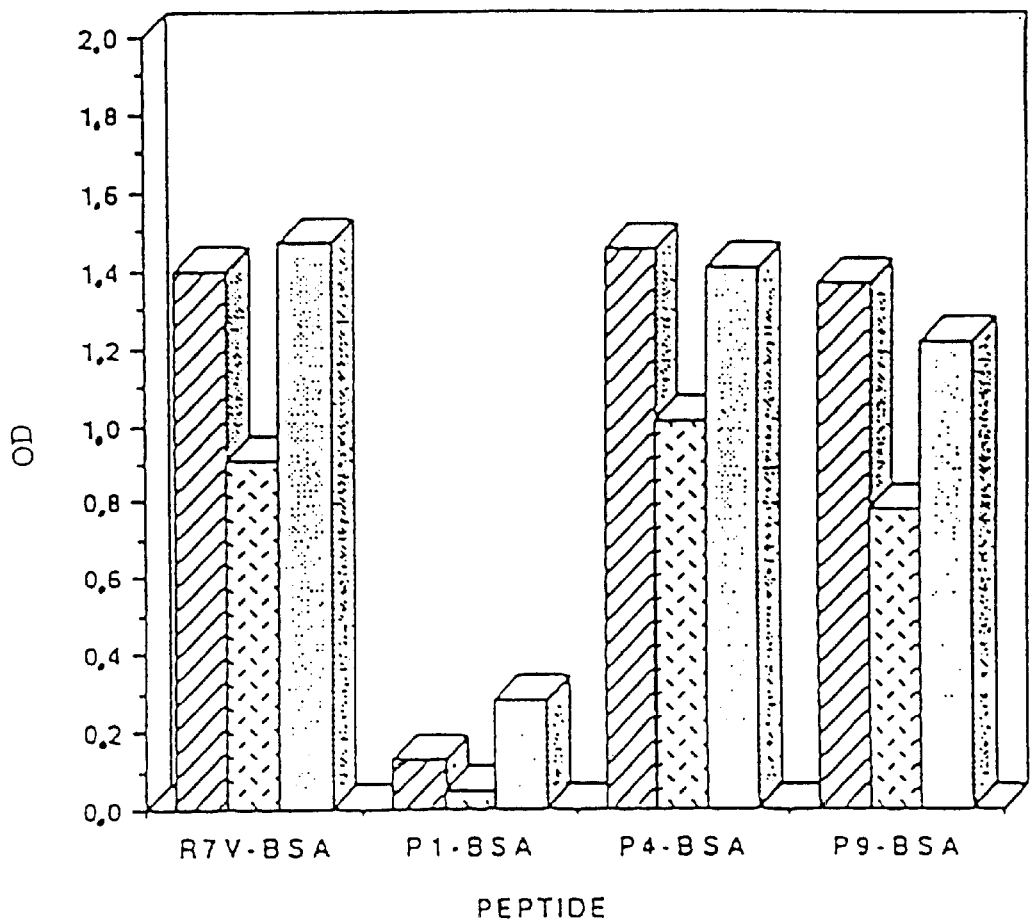
Figure 3B:
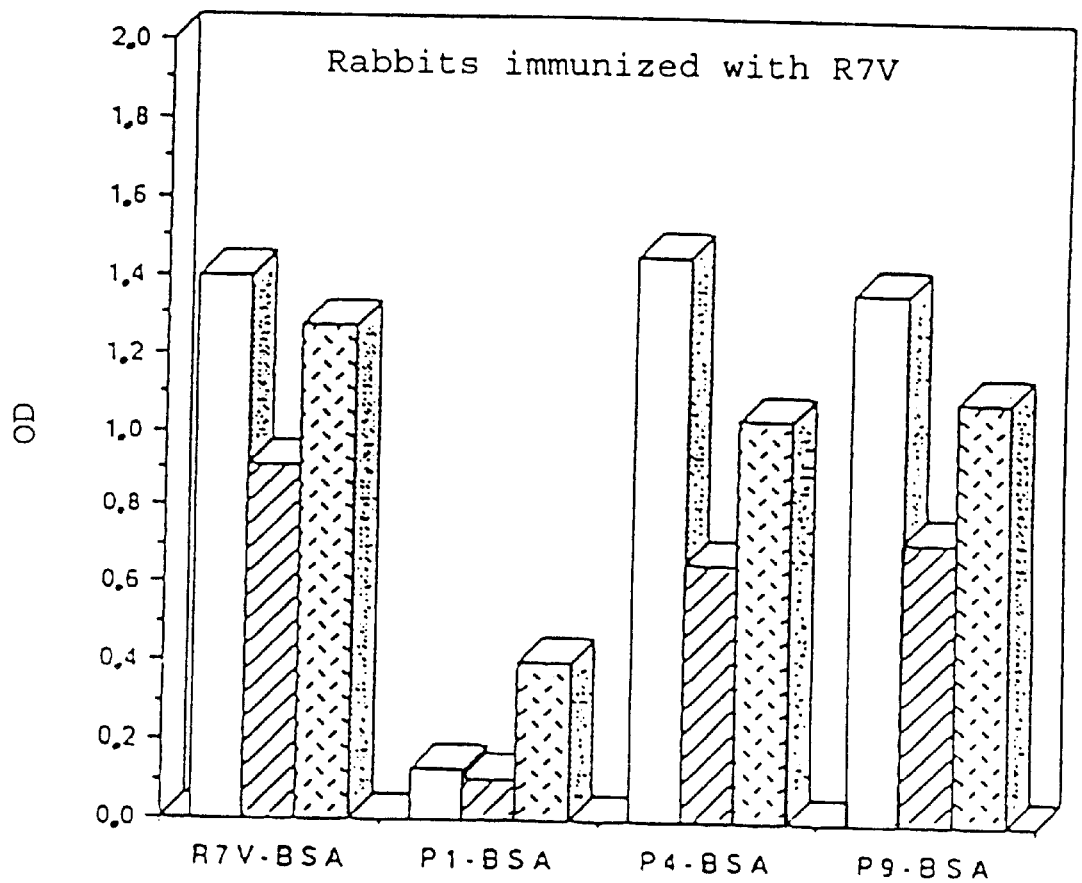
Figure 3C:
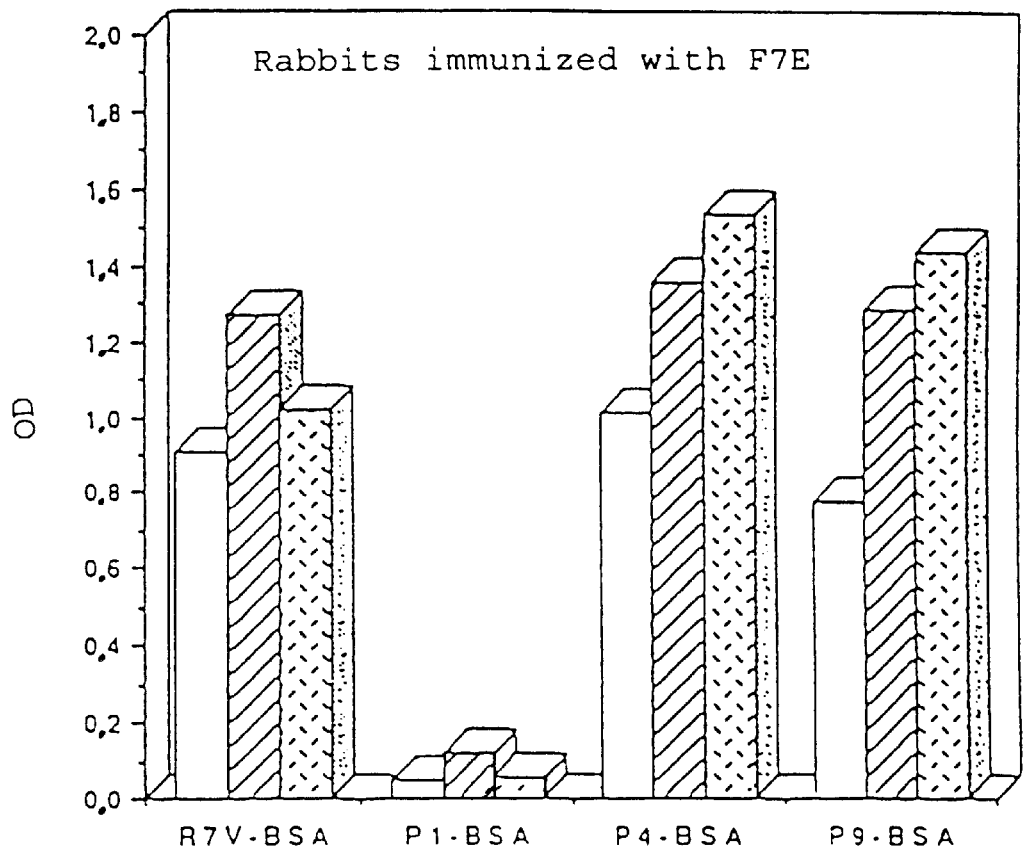
Figure 3D:
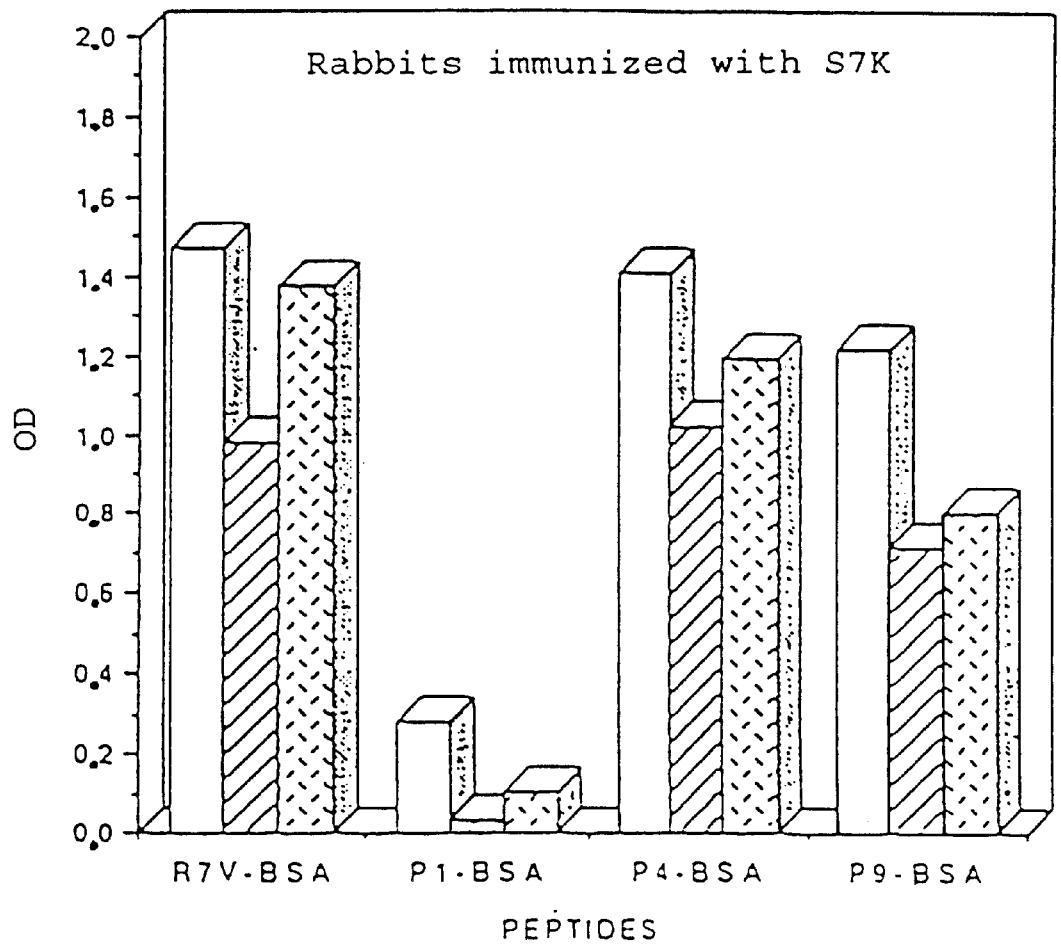
Figure 4:
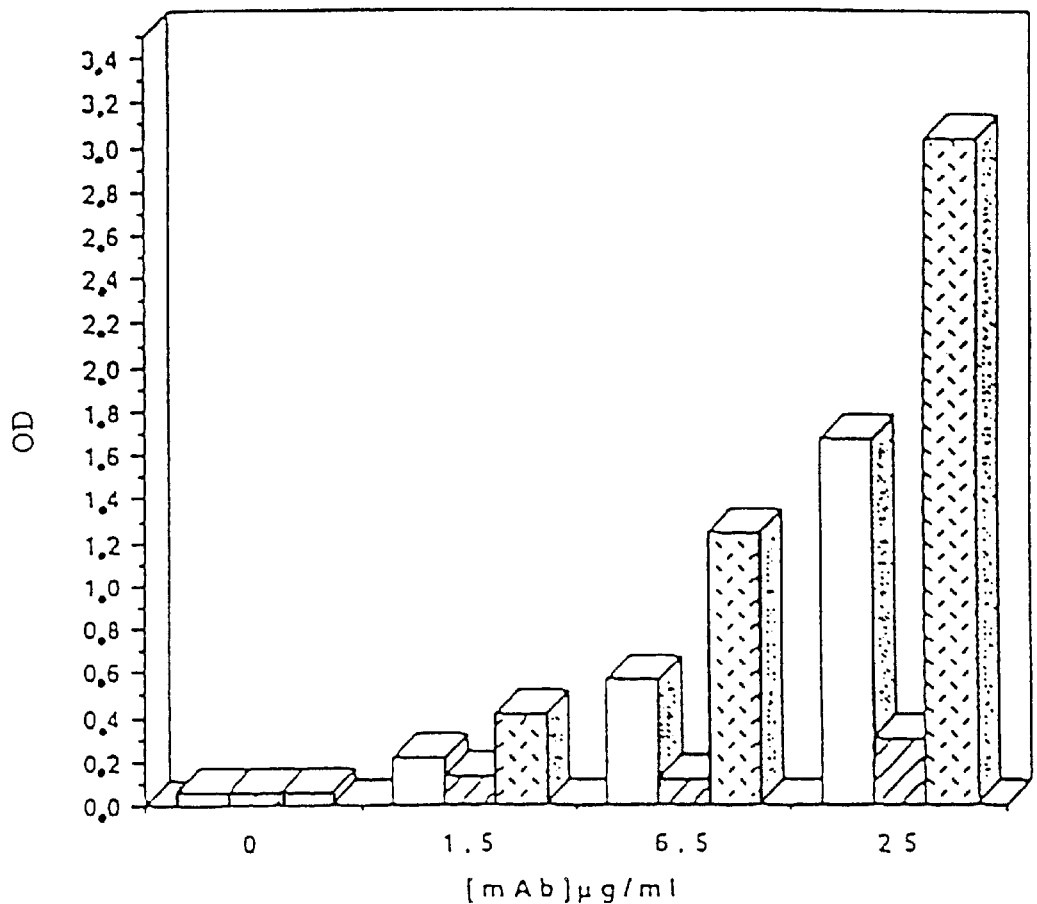
Figure 5:
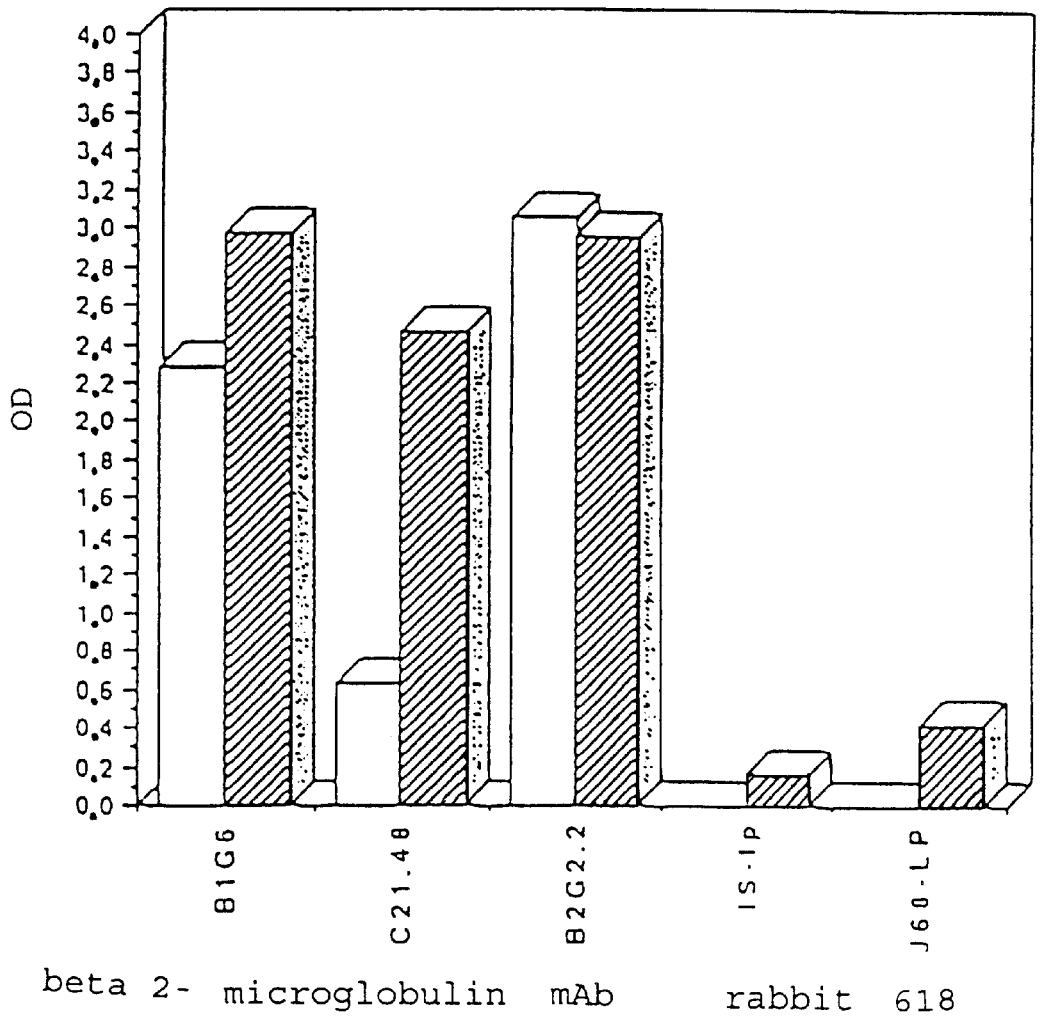

In the accompanying figures,

FIGS. 1A and 1B represent ELISAs showing the reactivity of the serum of a rabbit immunized with R7V-KLH for various antigens, FIG. 2 represents the ELISA showing the reactivity of the antiserum of a rabbit immunized with in particular β2m, FIGS. 3A to 3D represent the ELISA between different antisera and selected peptides, FIG. 4 represents the ELISA for R7V with different anti-β2m antibodies, FIG. 5 represents the ELISA for R7V-BSA and β2m with anti-β2m antibodies and rabbit sera, FIGS. 6 to 13 represent diagrams showing the effect of the sera of different patients on the neutralization of different isolates of the HIV virus on MT4 and PBL.

EXAMPLE 1

This example makes it possible to demonstrate the immune response of rabbits against selected peptides coupled to a carrier protein.

The peptide antigen 7AA is coupled to KLH (Key-hole Limpet Hemocyanin) and injected into rabbits in the presence of complete Freund's adjuvant.

The animals are immunized in the presence of complete Freund's adjuvant at D0, D14, D28, D42 and trial bleedings are carried out before immunization on days 35, 49, 56 and 70.

The peptides used are: RV7-KLH, S7K-KLH and F7E-KLH

The peptide R7V (RTPKIQV) (SEQ ID NO:4) was extended by 2 amino acids in order to allow the coupling. The structure used as immunogen is RTPKIQVGY (SEQ ID NO:23).

The antibodies of the rabbits immunized 618 were measured by ELISA, where the peptide coupled to various carrier proteins was used at the bottom of the well (either coupled to KLH, to BSA (Bovine Serum Albumin) or MAP (Multiple Antigenic Peptide)).

The diagrams represent the results obtained at 2 dilutions d100 and d1000, that is to say a 1/100 and 1/1000 dilution of the sera, or at different times.

The ELISA method is applied in the following manner:

ELISA method

1) Attachment of the antigen onto a 96-well plate (Immulon IV-Dynatech)
   dilute the antigen in carbonate buffer pH 9.6→(Ag) final=1 µg/ml
   distribute 100 µl/well, that is to say 100 ng/well
   incubate 2 h at 37° C. or overnight at 4° C. (humid atmosphere).
2) Washes
   5 washes with a solution of PBS/Tween 20 at 0.05%.
3) Saturation of the wells
   distribute 300 µl/well of a solution of PBS/horse (or bovine) serum at 10%
   incubate 1 h at 37° C. (in a humid atmosphere).
4) Washes (identical to point 2)
5) Incubation with specific antisera
   dilute the serum (1/50, 1/100, 1/1000) with PBS-10% horse serum
   distribute 100 µl/well and incubate 1 h at 37° C. (in a humid atmosphere).
6) Washes (identical to point 2)
7) Incubation with the second antibody (sheep Ig's to human Ig's coupled to peroxidase)
   dilute the second antibody 2/1000 in PBS/horse serum 10%
   distribute 100 µl/well and incubate 1 h at 37° C. (in a humid atmosphere).
8) Washes (identical to point 2)
9) Visualization with OPD
   dissolve 10 mg OPD in 25 ml of phosphocitrate buffer (0.1 M, pH 5.5)

add at the last moment 10 μl H$_2$O$_2$ distribute 100 μl/well and incubate 30 min in the dark at room temperature (may be read at 405 nm)

stop the reaction with 50 μl H$_2$SO$_4$ 12.5%.

10) Reading at 492 nm.

FIGS. 1A and 1B show results obtained with the rabbit 618 immunized with R7V-KLH.

An anti-R7V reactivity appears clearly as a differential between R7V-BSA and BSA compared with R7V-KLH and KLH where the anti-R7V reactivity is masked by the anti-KLH response of the serum. It should be noted that the anti-R7V reactivity is stronger at D68 than at D132.

The specificity of the reaction is greater if the BSA protein is used.

FIG. 2 again shows good recognition of the original protein, β2m.

The antisera of immunized rabbits demonstrate a high reactivity with R7V-BSA as well as with the original peptides called P1, P4 and P9 which were used to select R7V, even though the reactivity with P1 is weaker (FIGS. 3A–3D).

FIG. 4 demonstrates that the recognition of R7V by B1G6 and B2G2.2 depends on the dose and that the recognition of C21.48 is not as good; accordingly, the mAbs B1G6 and B2G2.2 will preferably be used to select equivalent peptides.

These results demonstrate that the R7V epitope, coupled to BSA, is capable of generating a good immune response.

EXAMPLE 2
Introduction of R7V into the V3 loop of HIV-1 LAV gp120
Construction of a recombinant provirus The objective of this example is to introduce the R7V sequence into the third variable region V3 of the HIV-1 LAV gp120.

Methods

Chimeric recombinant viruses were constructed by PCR-directed mutagenesis. Two constructs based on the R7V sequence and HIV-1 LAV were obtained, in which seven amino acids of the V3 region of gp120 have been replaced by the R7V sequence. The positions of the mutated sequences are shown in the following table:

for the PLG construct. In the second stage, two PCR products for each construct were mixed and amplified using the primers containing the BglII restriction sites. The RPL and PLG fragments were cleaved by the enzyme BglII and inserted into the vector Bluescript containing the EcoRI$_{5278}$-XhoI$_{8401}$ fragment of HIV-1 LAV, cleaved by BglII. In addition to the R7V sequence, the amplification primers contained modifications in the nucleotide sequence leading to the appearance of new BamHI and MluI restriction sites in the RPL and PLG constructs respectively, without additional modifications in the amino acid sequence. The new restriction sites were used to screen the mutated sequences. Finally, the EcoRI$_{5278}$-XhoI$_{8401}$ fragments of HIV-1 LAV containing the RPL and PLG constructs were inserted into the plasmid pNL4-3 by homologous recombination using the EcoRI and XhoI restriction sites. The constructs were checked by restriction enzyme analysis.

Transfection of eukaryotic cells

The plasmid DNA of 200 ml of *E. coli* TG1 was extracted and purified by the Qiagen midipreparation kit. The semiconfluent cultures of COS cells (≅4×10$^6$) were transfected with 7 μg of plasmid by the calcium coprecipitation technique. The next day, the monolayers of cells were treated with glycerol and placed in coculture with a CEM cell line or with primary blood lymphocytes activated by PHA (PBL, 10$^6$ cells/ml) obtained from a healthy donor. The CEM or PBL cells were separated from the COS cells in monolayers two days later and cultured separately.

Production of virus 1 ml of free cell supernatant obtained from the COS or PBL cells was ultracentrifuged and the virus sedimented was checked by the standard reverse transcriptase reaction. In some experiments, 100 μl of cell supernatant was tested for the production of the p24gag protein.

```
HIV-1 LAV (V3) (SEQ ID NO:24)  NNNTRKSIRIQRGPGRAFVT

R7V (SEQ ID NO:4)                        RTPKIQV    (1) RPL

R7V (SEQ ID NO:4)                        RTPKIQV    (2) PLG
```

The EcoRI$_{5278}$-XhoI$_{8401}$ fragment of HIV-1 LAV cloned into the vector Bluescript was used as template for subsequent constructs. In the first stage, the DNA fragments flanked by primers containing the BglII restriction site at one end and the nucleotide sequence encoding R7V at the other end were synthesized for the RPL and PLG constructs by PCR amplification. The mutagenesis oligonucleotides used consisted of a (+) primer (SEQ ID NO:25) ACACCAAA-GATACAAGTTGTTACAAATAGGAAAA and a (−) primer (SEQ ID NO:26) TTGTATCTTTGGTGTTCTCTG-GATCCGGATACTTT for the RPL construct and of a (+) primer (SEQ ID NO: 27) CGTACACCAAAAATCCAG-GTCCAGAGAGGACCA and a (−) primer (SEQ ID NO: 28) GATTTTTGGTGTACGCGTATTGTTGTTGGGTCT

| Transfection of the COS cells and coculture with the CEM cells | | | |
|---|---|---|---|
| | Reverse transcriptase activity (cpm/ml) | | |
| D. post-transf. | RPL 1 | PLG 2 | NL 4-3 |
| 5 | 7282 | 7730 | 45838 |
| 9 | 3282 | 5302 | 326618 |
| 13 | 382 | 630 | ND |
| 16 | 200 | 300 | ND |

$4 \times 10^6$ COS cells were transfected per 7 µg of plasmid by the calcium coprecipitation technique. The CEM cells were then added in an amount of $4 \times 10^5$ cells/ml in a final volume of 5 ml. After two days of coculture, the CEM cells in suspension were separated from the COS cells in a monolayer. The reverse transcriptase activity in the CEM culture supernatants is given in cpm/ml.

Infection of the PBLs

| D. post-inf. | Reverse transcriptase activity (cpm/ml) | | |
|---|---|---|---|
| | RPL 1 | PLG 2 | NL 4-3 |
| 4 | 734 | 782 | 20008 |
| 7 | 202 | 216 | |
| 10 | 262 | 282 | |
| 14 | 454 | 262 | |
| 17 | 204 | 138 | |

| | RPL 1 | + PBL | PLG 2 | + PBL 2 |
|---|---|---|---|---|
| 1 | 350 | 336 | 276 | 636 |
| 24 | 230 | 282 | 296 | 284 |
| 27 | 588 | 510 | 620 | 980 |

$2.5 \times 10^6$ PBLs were infected with the acellular supernatants of Dec. 19, 1994 obtained after transfection (Table 1) in an amount of 5000 cpm/$10^6$ PBL. On day 17 post-infection, $2 \times 10^6$ newly isolated PBLs were added to $2 \times 10^6$ infected PBLs (RPL 1+PBL, PLG 2+PBL). The reverse transcriptase activity in the culture supernatants is given in cpm/ml.

Transfection of the COS cells and coculture with PBLs

| D. post-transf. | Reverse transcriptase activity (cpm/ml) | | | |
|---|---|---|---|---|
| | PLG 2-25 | PLG 2-30 | PLG 2-95 | NL 4-3 |
| 3 | 2500 | 8400 | 3500 | 2150 |
| 7 | 446 | 398 | 582 | 53000 |
| 10 | 174 | 336 | 306 | 74000 |
| 14 | 730 | 834 | 482 | 45778 |

| | R.T. activity (cpm/ml) | |
|---|---|---|
| | RPL 1 | PLG 2 |
| 3 | 20338 | 22000 |
| 7 | 682 | 418 |
| 11 | 552 | 466 |

$4 \times 10^6$ COS cells were transfected with 7 µg of plasmid by the calcium coprecipitation technique. The PBL cells stimulated with PHA were then added in an amount of $10^6$ cells/ml in a final volume of 5 ml. After two days of coculture, the PBLs in suspension were separated from the COS cells in a monolayer. The reverse transcriptase activity in the PBL culture supernatants is given in cpm/ml.

EXAMPLE 3

The aim of this example is to use the selected peptides to detect, in the serum of the patients, antibodies which are potentially inhibitors of HIV (anti-β2-microglobulin antibodies) and in particular to demonstrate the presence of protective antibodies in the serum of patients who do not progress. "Patients who do not progress" or "NP" designate patients who have been seropositive for more than 10 years and who have not developed AIDS, in particular whose T4 cell level is normal.

Materials and methods

1/ The peptides used were synthesized and coupled to BSA by Néosystem (France).

2/ The sera of the patients are stored at −20° or 80° C. before their use in Elisa.

3/ The second antibodies to human or rabbit Ig's were obtained from Amersham (France). OPD is obtained from Sigma (France).

ELISA with the sera of seropositive patients

1/ Presence of anti-R7V antibodies in the serum of the patients (titre 1/100 and 1/1000).

2/ Of the 46 sera tested from people who do not progress (no viral replication in culture), 16 sera are positive for R7V (37%), 27 remain negative to 1/100 (63%) and 3 sera are impossible to determine (Table 1).

3/ Of the 46 patients who do not progress, 34 were tested for the detection of anti-peptide antibodies: R7V, P1, P4, P9. 14 sera are positive for at least one peptide (51.8%) and 13 remain negative to 1/100. Four sera could not be classified positive or negative (Table 2).

TABLE 1

ELISA R7V with NP sera

| NAME | NUMBER | R7V |
|---|---|---|
| ARA GE | 950 | Negative |
| ARG CH | 150 | Not determined |
| AUD PA | 1509 | Negative |
| BAT AL | 134 | Negative |
| BAR JE | 342 | Positive |
| BER AL | 704 | Positive |
| BER SE | 1337 | Negative |
| BES LA | 287 | Positive |
| BEU PH | 5.33 | Negative |
| BOR EM | 194 | Negative |
| BOU NA | 5.36 | Positive |
| BRE FR | 20.2.95-5.32 | Negative |
| CAB MI | 573 | Negative |
| CAU BE | 167/1113 | Negative |
| CHI OL | 353A | Negative |
| COU DA | 1531 | Negative |
| DIB AN | 872 | Positive |
| DUR JE | 937 | Positive |
| GAR AI | 986 | Negative |
| GAS MA | 549 | Negative |
| GUI JE | 60 | Positive |
| GUI PI | 26.1.95-2.9 | Negative |
| HAN SO | 169/5.31 | Positive |
| HOL CH | 4.25 | Negative |
| IBE JU | 6.39 | Positive |
| IMB PI | 327 | Not determined |
| MAG HE | 143 | Negative |
| MAN GU | 26.1.95-2.8 | Negative |
| MAN RO | 89 | Positive |
| MAN XA | 730 | Negative |
| MART DO | 1412 | Negative |
| MAS SU | 115 | Negative |
| MEN JO | 622/1382 | Positive |
| MON NA | 1010 | Negative |
| NIC GE | 294 | Negative |
| OUM NA | 1386 | Negative |
| PAR FR | 23.1.95-1.7 | Negative |
| MEN JO | 622/1382 | Positive |

TABLE 1-continued

ELISA R7V with NP sera

| NAME | NUMBER | R7V |
|---|---|---|
| POI LI | 3.14 | Negative |
| PUJ MA | 23.1.95-1.2 | Negative |
| QUI AL | 23.1.95-1.5 | Negative |
| RIO EM | 3.16 | Negative |
| RIS HE | 2.10 | Negative |
| ROY CH | 5.35 | Not determined positive |
| SAL YA | 13.3.95 | Negative |
| SAN NA | 2.11 | Negative |
| SAU CH | 171/4.27 | Positive |
| TEM ST | 1343 | Positive |
| VIA JE | 701 | Not determined |
| ZUM AM | 333 | Positive |

TABLE 2

ELISA for the peptides with the NP sera

| NAME | NUMBER | POSITIVE/ NEGATIVE | R7V | P1 | P4 | P9 |
|---|---|---|---|---|---|---|
| BEU PH | 5.33 | Negative | | | | |
| BOU NA | 5.36 | Positive | Pos. | Pos. | Pos. | Neg. |
| BRE FR | 20.2.95–532 | Positive | Neg. | Pos. | Pos. | Neg. |
| CIF FR | 6.38 | Negative (?) | | | | |
| ETC MA | 6.45 | (?) | | | | |
| GEM SA | 6.40 | (?) | | | | |
| GUI JE | 60 | Positive | Pos. | Pos. | Neg. | Neg. |
| GUI PI | 26.1.95–2.9 | Negative | | | | |
| HAN SO | 169/5.31 | Positive | Pos. | Pos. | Neg. | Pos. |
| HOL CH | 4.25 | Negative | | | | |
| IBE JU | 6.39 | Positive | Pos. | Pos. | Neg. | Neg. |
| LED DO | 4.23 | Positive | Neg. | Pos. | Neg. | Neg. |
| MAN GU | 26.1.95–2.8 | Negative | | | | |
| MEN JO | 622/1382/6.43 | Positive | Pos. | Pos. | Pos. | Pos. |
| MOR JE | 5.37 | Positive | Neg. | Neg. | Pos. | Neg. |
| PAR FR | 23.1.95–1.7 | Negative | | | | |
| PAT MA | 166 | Positive | Neg. | Neg. | Pos. | Neg. |
| PIC CH | 2.12 | (?) | | | | |
| POI LI | 3.14 | Negative | | | | |
| PUJ MA | 23.1.95–1.2 | Negative | | | | |
| QUI AL | 23.1.95–1.5 | Negative | | | | |
| RIO EM | 3.16 | Negative | | | | |
| RIS HE | 2.10 | Negative | | | | |
| ROY CH | 5.35 | Positive | Pos. (?) | Pos. | Neg. | Neg. |
| SAL YA | 13/3.95 | Negative | | | | |
| SAN NA | 2.11 | Negative | | | | |
| SAP MA | 4.21 | (?) | | | | |
| SAU CH | 171/4.27 | Positive | Pos. Pos. (?) | | Pos. | Pos. |
| SEN AN | 4.28 | Positive | Neg. | Pos. | Neg. | Neg. |
| TEM ST | 5.34 | Positive (?) | Pos. | (?) | (?) | (?) |
| ZUM AM | 333 | Positive | Pos. | (?) | (?) | (?) |

(?) Not determined

EXAMPLE 4

The following trials made it possible to detect antibodies neutralizing various HIV isolates, particularly BRU and NDK, in patients who do not progress, the same patients having anti-R7V antibodies. This makes it possible to show a good correlation between the neutralizing and protective character against HIV of the antibodies generated by the treatments according to the invention.

Materials and methods

Culture of the MT4 cells

The MT4 cells are immortalized cells (CD4+) which are very sensitive to the cytopathogenic effect of HIV-1, originally derived from a T leukaemia in adults. The cells are cultured in the presence of RPMI medium supplemented with 10l of foetal calf serum, 1% of glutamine and 1k of antibiotic.

Culture of the PBLs

The lymphocytes are stimulated for 3 days with phytohemagglutinin P (PHA P) in complete RPMI medium comprising 10% of foetal calf serum, 1% of glutamine, 1% of antibiotic, 2 $\mu$g/ml of polybren, 20 IU/ml of interleukin 2 (IL-2). The cells are then washed and cultured in an amount of $10^6$ cells/ml in complete RPMI medium.

Neutralization tests

The sera are decomplementized and filtered before they are used in the tests.

Neutralization on MT4

The sera are diluted in 24-well plates (Costar) in a total volume of 0.8 ml. the HIV-1 BRU viruses (100 $\mu$l of a 10-l dilution of the stock solution) or HIV-1 NDK viruses (100 $\mu$l of a $10^{-3}$ dilution of the stock solution) are added and the mixture is incubated for 1 h 30 min at 37° C. and 5% CO2. The cells are then distributed in an amount of 200 $\mu$l/well and $1.5\times10^6$ cells/ml. Three days after the infection, the cultures are diluted (⅓) with 10% RPMI medium. The infection of the cells with the HIV-1 viruses is monitored every day under a microscope by observing the formation of syncitia (multinucleated giant cells). The neutralization of the viruses with the different sera is defined by the absence (–) of syncitia or very few syncitia (+/–) compared with the formation of syncitia which is induced by the (+) prototype HIVs.

Neutralization on PBL

The sera (50 $\mu$l) are mixed with the HIV-1 BRU viruses (50 Al of a 2 x 10-1 dilution of the stock solution) in 96-well plates and placed for 1 h 30 min at 37° C. and 5% CO2. The mixture is then added to $10^6$ PBLs in 24-well plates (Costar) and the culture is maintained for 3 days at 37° C. and 5% CO2. The cells are then washed and cultured in an amount of $10^6$ cells/ml in 25 $cm^2$ culture flasks. The production of virus is monitored every 3 or 4 days by assaying the "Reverse Transcriptase" enzymatic activity.

Assay of the "Reverse Transcriptase" (RT) activity

One ml of centrifuged culture supernatant (1500 rpm), RT, 10 min) is concentrated 100 fold by ultracentrifugation (95000 rpm, 4° C., 5 min) on a TL 100 rotor (Beckman). The pellet obtained is taken up in 10 $\mu$l of NTE buffer—0.1% Triton X100. The enzymatic reaction is carried out in 50 $\mu$l of the following reaction mixture: 50 mM Tris pH 7.8; 20 mM $MgCl_2$; 20 mM KCl: 2 mM dithiothreitol; Oligo dT 12-18 0.25 OD/ml: poly rA 0.25 OD/ml and 2.5 $\mu$Ci of $^3$HdTTP. After incubating for 1 h at 37° C., the reaction products are precipitated with 20% trichloroacetic acid, filtered on Millipore membranes and the β radioactivity is measured. The results are expressed in CMP/ml.

Report for the neutralization experiments

Antibodies directed against the peptide R7V were detected in the sera of HIV +patients by means of a specific ELISA developed by the Applicant. A search was made in these sera for the existence of a neutralizing activity directed against the two prototype virus strains HIV-1 BRU and NDK. Two neutralization tests were carried out, one on an MT4 cell line (followed by the formation of syncitia) and the other on healthy peripheral blood lymphocytes, PBL (followed by the "Reverse Transcriptase" enzymatic activity).

Results obtained on MT4

Of the 13 patients tested, a neutralizing serum activity was detected for 6 of them (Tables 3 to 5):

two sera neutralize HIV-1 NDK:
  ZUM AM (ELISA positive)
  COC PH (ELISA negative)
two sera neutralize HIV-1 BRU:
  MEC EV (ELISA positive)
  OUA VE (ELISA negative)
two sera neutralize HIV-1 BRU and HIV-1 NDK:
  SAU CH (ELISA positive)
  BUB JE (ELISA positive)

Results obtained on PBL

The experiment was carried out with the sera of MEC EV, SAU CH and BUB JE (1/50) as well as with a serum from a seronegative individual. No neutralizing activity was detected for the SAU CH serum as well as for the seronegative serum. On the other hand, a neutralizing activity against the two prototype viruses HIV-1 BRU and NDK was detected for the sera MEC EV and BUB JE (FIGS. 6 to 13).

EXAMPLE 5

Method which makes it Possible to detect equivalent peptides

Effect of selected peptides on the neutralization of HIV-1 NDK by anti-B1G6 92 monoclonal antibodies Protocol The peptides at a concentration of 100 $\mu$g/ml or 50 $\mu$g/ml (40 $\mu$l or 20 $\mu$l of the stock solution and 5 mg/ml) are preincubated with 5 $\mu$g/ml of B1G6 (10 $\mu$l of a stock solution at 1 mg/ml) in a total volume of 110 $\mu$l for 2 hours, in tubes on a water bath at 37° C., with gentle stirring. Next, HIV-1 NDK is added (100 $\mu$l of a $2\times10^{-4}$ dilution of a stock solution and the tubes are incubated for 1 hour at 37° C. on a water bath. The tubes are then separated into two and each 100 $\mu$l is added to $10^6$ PBLs on a 24-well plate. The cells are cultured for 3 days at 37° C. under an atmosphere with 5% $CO_2$. On day 3, the cells are washed, placed in culture and propagated for at least 20–25 days in a 25 cm³ round-bottomed flask. The production of virus is monitored every 3 or 4 days by the assay of reverse transcriptase (RT).

Results

The peptides R7V and F7E can cancel the neutralizing effect of the monoclonal antibody B1G6 on the productin of HIV-1 NDK by the PBLs. The sequence of the R7V peptide was modified and among the 6 new peptides (185, 186, 187, 188, 189, 190), 3 lost the canceling effect of R7V: peptides 185, 189 and 190.

TABLE 3

| | | NDK Day/Post-infection | | | | | | | | | | | |
|---|---|---|---|---|---|---|---|---|---|---|---|---|---|
| | | D4 | | | D5 | | | D6 | | | D7 | | |
| | | 1/25 | 1/50 | 1/100 | 1/25 | 1/50 | 1/100 | 1/25 | 1/50 | 1/100 | 1/25 | 1/50 | 1/100 |
| HIV+ | ZUM AM | − | − | − | − | − | − | − | − | − | − | − | + |
| | HAN SO | − | − | − | + | − | − | + | +/− | +/− | + | + | + |
| | SAU CH | − | − | − | + | + | + | + | + | + | + | + | + |
| | MEN JO | − | − | − | +/− | − | +/− | + | +/− | + | + | +/− | + |
| | PAT MA | +/− | − | − | +/− | + | − | +/− | +/− | − | +/− | +/− | − |
| | COC PH | − | − | − | − | − | + | − | − | + | − | − | + |
| HIV− | SER C | − | − | − | + | + | + | + | + | + | + | + | + |
| | DOU S | − | − | − | + | + | + | + | + | + | + | + | + |
| | AUB V | − | − | − | + | + | + | + | + | + | + | + | + |
| NDK $10^{-4}$ | | | +/− | | | + | | | + | | | + | | |

TABLE 4a

| | | NDK Day/Post-Infection | | | | | | | |
|---|---|---|---|---|---|---|---|---|---|
| | | D4 | | D5 | | D6 | | D7 | |
| | | 1/50 | 1/100 | 1/50 | 1/100 | 1/50 | 1/100 | 1/50 | 1/100 |
| HIV+ | ZUM AM | − | +/− | + | + | + | + | + | + |
| | HAN SO | + | +/− | + | + | + | + | + | + |
| | SAU CH | + | + | + | + | + | + | + | + |
| | MEN JO | + | + | + | + | + | + | + | + |
| | MEC EV | +/− | − | +/− | + | + | + | + | + |

TABLE 4a-continued

| | | NDK Day/Post-Infection | | | | | | | |
|---|---|---|---|---|---|---|---|---|---|
| | | D4 | | D5 | | D6 | | D7 | |
| | | 1/50 | 1/100 | 1/50 | 1/100 | 1/50 | 1/100 | 1/50 | 1/100 |
| | PAT MA | +/− | +/− | +/− | + | + | + | + | + |
| | COC PH | +/− | − | +/− | − | + | + | + | + |
| HIV− | AUB V | + | +/− | + | + | + | + | + | + |
| | NDK $10^{-4}$ | | + | | + | | + | | + |

TABLE 4b

| | | BRU Day/Post-infection | | | | | | | |
|---|---|---|---|---|---|---|---|---|---|
| | | D4 | | D5 | | D6 | | D7 | |
| | | 1/50 | 1/100 | 1/50 | 1/100 | 1/50 | 1/100 | 1/50 | 1/100 |
| HIV+ | ZUM AM | +/− | +/− | +/− | + | + | + | + | + |
| | HAN SO | +/− | +/− | +/− | + | + | + | + | + |
| | SAU CH | + | + | + | + | + | + | + | + |
| | MEN JO | − | +/− | +/− | +/− | + | + | + | + |
| | MEC EV | − | − | − | − | − | + | − | + |
| | PAT MA | +/− | − | +/− | +/− | + | + | + | + |
| | COC PH | − | +/− | +/− | + | + | + | + | + |
| HIV− | AUB V | + | + | + | + | + | + | + | + |
| | BRU $10^{-2}$ | | +/− | | + | | + | | + |

TABLE 5a

| | | NDR Day/Post-infection | | | | | | | | | | |
|---|---|---|---|---|---|---|---|---|---|---|---|---|
| | | D4 | | | D5 | | | D6 | | | D7 | | |
| | | 1/25 | 1/50 | 1/100 | 1/25 | 1/50 | 1/100 | 1/25 | 1/50 | 1/100 | 1/25 | 1/50 | 1/100 |
| HIV+ | AUM AM | − | +/− | +/− | − | +/− | + | − | + | + | − | + | + |
| | MEC EV | − | − | − | + | +/− | − | + | + | + | + | + | + |
| | SAU CH | − | +/− | +/− | − | − | − | − | − | +/− | − | − | + |
| | OUA VE | − | − | +/− | − | +/− | + | +/− | + | + | + | + | + |
| | QUI AL | +/− | +/− | +/− | + | + | + | + | + | + | + | + | + |
| | BUB JE | +/− | − | +/− | − | +/− | +/− | − | + | + | − | + | + |
| | PUJ MA | +/− | +/− | +/− | +/− | +/− | + | +/− | +/− | + | +/− | + | + |
| | SEN AN | +/− | +/− | + | + | + | + | + | + | + | + | + | + |
| | RIO EM | +/− | +/− | +/− | + | + | + | + | + | + | + | + | + |
| HIV− | AUB V | + | + | + | + | + | + | + | + | + | + | + | + |
| | NDK $10^{-4}$ | | +/− | | | + | | | + | | | + | |

TABLE 5b

| | | D4 | | | D5 | | | D6 | | | D7 | | |
|---|---|---|---|---|---|---|---|---|---|---|---|---|---|
| | | 1/25 | 1/50 | 1/100 | 1/25 | 1/50 | 1/100 | 1/25 | 1/50 | 1/100 | 1/25 | 1/50 | 1/100 |
| HIV+ | ZUM AM | − | +/− | + | + | + | + | + | + | + | + | + | + |
| | MEC EV | − | − | − | − | − | − | − | − | − | − | − | +/− |
| | SAU CH | − | − | − | − | − | − | − | − | + | − | − | + |
| | OUA VE | − | − | − | − | − | +/− | − | + | + | − | + | + |
| | QUI AL | − | − | − | − | − | + | + | +/− | + | + | + | + |
| | BUB JE | − | − | − | − | − | − | − | +/− | +/− | − | + | + |
| | PUJ MA | − | − | +/− | +/− | + | + | + | + | + | + | + | + |
| | SEN AN | − | − | +/− | | +/− | +/− | + | + | + | + | + | + |
| | RIO EM | +/− | +/− | +/− | + | + | + | + | + | + | + | + | + |
| HIV− | AUB V | + | + | +/− | + | + | + | + | + | + | + | + | + |
| | BRU 10⁻³ | | + | | | + | | | + | | | + | |

EXAMPLE 6
Correlation between the presence of anti-R7V antibodies and the progression of the disease Serum samples from 90 patients infected with HIV are used. They are distributed as follows: 28 patients who have been asymptomatic for more than 3 years, 24 long-term survivors and 38 patients suffering from Aids. A control group consisting of 69 seronegative volunteer donors was obtained from the blood bank.

The lymphocytes were counted by indirect immunofluorescence and analyzed by Epic Profile (Coultronics, Margency, France). The β2m serum levels were measured by immunodiffusion (El Nanorid Kit). The p24 antigen levels were tested by the Coulter p24 detection kit (Coultronics, Margency, France).

The serum concentrations of anti-R7V antibodies are detected by ELISA. The results are expressed as concentration of B1G6 monoclonal antibody equivalent in μg/ml.
Neutralization trial The human sera are decomplementized and diluted up to 200 μg/ml or 100 μg/ml of B1G6 equivalent. 50 μl of HIV containing 100 TCID$_{50}$ are preincubated with 50 μl of dilute serum (total volume 100 μl) in a 96-well plate at 37° C. and 5% CO$_2$ for 90 min. The reaction mixture containing the viruses and the serum is diluted twice after addition of 8×10⁴ MT4 cells (final dilution of the sera from 1/120 to 1/20) and three times again three days after the infection. The fusogenic effect of HIV in the MT4 lines, that is to say the formation of syncytia as an indicator of infection by the virus, is monitored for 7 days in the culture wells. The Reverse Transcriptase activity is measured in 400 μl of supernatant free of cell, 7 days after the infection.

The mean value of the anti-R7V antibody levels is calculated for each patient and for each group. The sera of people infected with HIV contain anti-R7V antibodies and the HIV seropositive sera show significantly higher concentrations of anti-R7V antibodies than seronegative sera. The anti-R7V antibody levels, expressed as B1G6 equivalent, range from 35 to 2558 μg/ml (n=90) and from 27 to 1790 μg/ml (n=69), respectively, in the groups infected with HIV and in the groups not infected with HIV.

The group with the HIV patients was then classified into three categories according to their clinical status: the group with those who do not progress (NP) consisting of the patients who have been seropositive for HIV for a long period and have been monitored in the laboratory for more than 3 years without Aids symptoms; the group with long-term survivors (LTS) consists of people who have had Aids for a long period, and finally a group which progresses consists of people suffering from Aids with a bad prognosis.

The anti-R7V antibodies are significantly increased in the asymtomatic group (from 91 to 2558 μg/ml) compared with the group which progresses (from 35 to 630 μg/ml) (p=0.001) whereas no significant difference is observed compared with the LTS group (from 59 to 1864 μg/ml). Likewise, the LTS group has higher anti-R7V levels than the group which progresses (p=0.004). Compared with the healthy subjects, there is no difference in the anti-R7V antibody level in the group which progresses.

In the group which progresses, a clear distinction can be made according to the anti-R7V antibody level between the subjects who die shortly after their last visit to the laboratory (from 35 to 508 μg/ml, n=23) and those still alive but ill (from 77 to 586 μg/ml, n=14) (p<0.03).

A longitudinal follow-up study was not able to establish a correlation between the anti-R7V antibody levels and other biological parameters such as total lymphocyte count, CD4 and CD8 cells, p24 and β2m in circulation.

It appears that the R7V level is stable over time in the NP patients, whereas it fluctuates in the LTS patients.

In order to link the ELISA test with a biological activity of the patient's serum, a neutralization test was carried out with two nonrelated viruses, the HIV-1 LAV strain and the highly cytopathogenic HIV-1 NDK strain, on indicator MT4 cells. The serum dilutions were adjusted in order to obtain 5 μg of B1G6 equivalent in the neutralization mixture. This concentration was defined as optimum for neutralizing the infection by the B1G6 antibodies. As seen in Table 5, 17 of the 18 sera selected prevent the infection of MT4 cells both by NDK and by LAV. To obtain 5 μg of B1G6 equivalent in culture, 13 of the 18 sera tested required a dilution less than 1/50. In order to eliminate nonspecific activities due to possible serum components, these sera with a low B1G6 equivalent level were diluted 1/100 and used in the neutralization trial. The quantity of B1G6 equivalent in culture was then less than 5 μg (from 2.5 μg/ml to 0.3 μg/ml). Nine of the 14 sera (64%) still neutralized both HIV strains, LAV and NDK, at a 1/100 dilution. Three sera from healthy donors used as controls show no neutralizing activity.

TABLE 5

| Dilutions of the serum at 5 μg of B1G6 equivalent in the trial | Number of sera which neutralize the two strains of HIV/total sera tested |
|---|---|
| dilution ≧ 1/50 | 5/5 |
| 1/50 > dilution ≧ 1/20 | 10/11 |
| dilution < 1/20 | 2/2 |
| TOTAL | 17/18 |

LEGEND TO THE FIGS.

LEGEND TO FIG. 1A

☑ J63 d100
☒ J132 d100

LEGEND TO FIG. 1B

☑ J63 d100
☒ J132 d100

LEGEND TO FIG. 2
ELISA with rabbit antiserum for R7V or β2m
rabbit 618 (immunization with R7V-KLH) serum dilution 1/100

■ IMMUNE SERUM
☐ J63 pi
☒ J132 pi

LEGEND TO FIG. 3A
ELISA with rabbit antiserum on wells coated with peptide

☑ rabbit 618 immunized with R7V
☑ rabbit 621 immunized with F7E
☐ rabbit 624 immunized with S7K LEGEND TO FIG. 3B
ELISA with sera of immunized rabbits ☐ rabbit 618
☑ rabbit 619
☒ rabbit 620

LEGEND TO FIG. 3C
ELISA with the sera of immunized rabbits

☐ rabbit 621
☑ rabbit 622
☒ rabbit 623

LEGEND TO FIG. 3D
ELISA with sera of immunized rabbits

-continued

LEGEND TO THE FIGS.

☐ rabbit 624
☑ rabbit 625
☒ rabbit 626

LEGEND TO FIG. 4
ELISA with B1G6, C21.43, B2G2.2 mAb for R7V

☐ B1G6
☑ C21.48
☒ B2G2.2

LEGEND TO FIG. 5
ELISA FOR R7V-BSA OR β2

☐ R7V
☑ BETA2m

Figure 6:
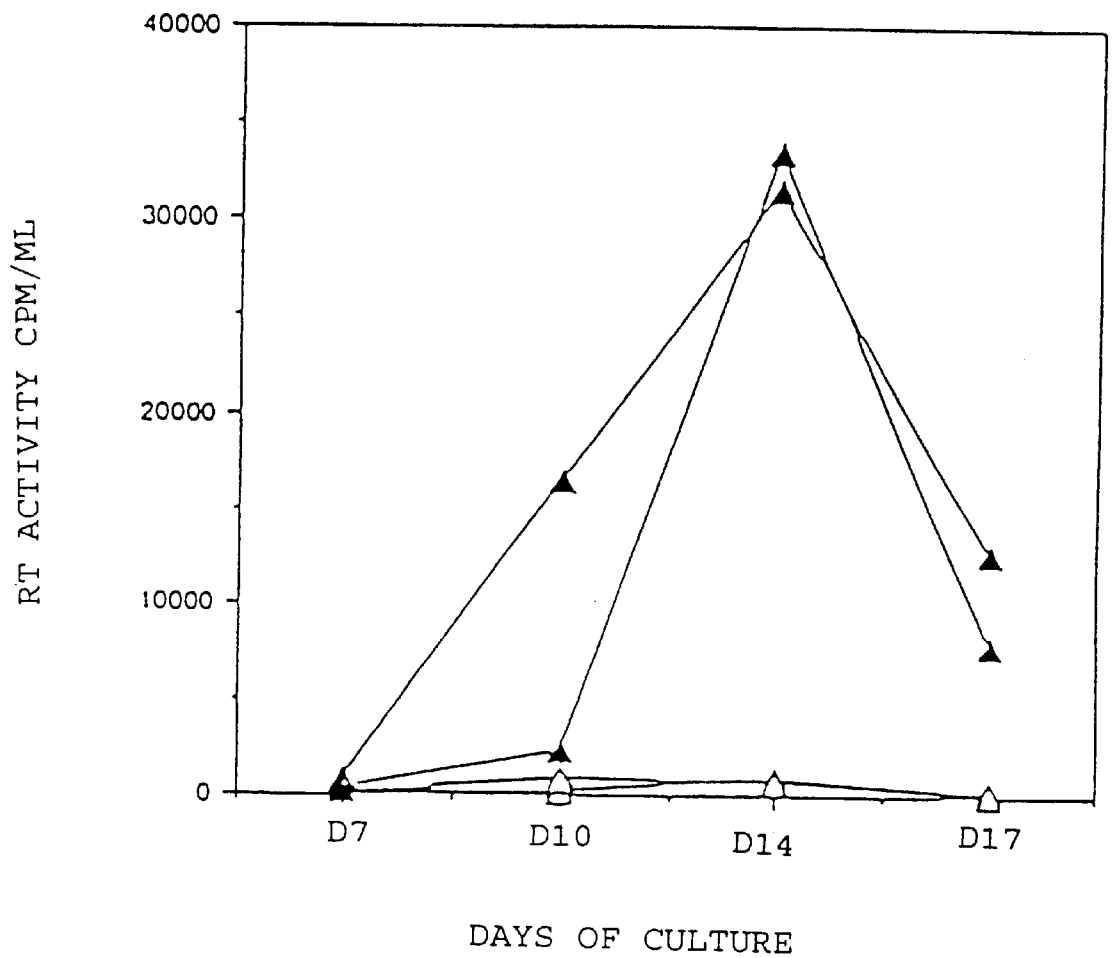

LEGEND TO FIG. 6
NEUTRALIZATION OF HIV-1 BRU-1 WITH THE SERUM MEC EV (1/50) ON PBL

—△— MEC EV 50
—△— MEC EV 50'
—▲— BRU
—▲— BRU'

Figure 7:
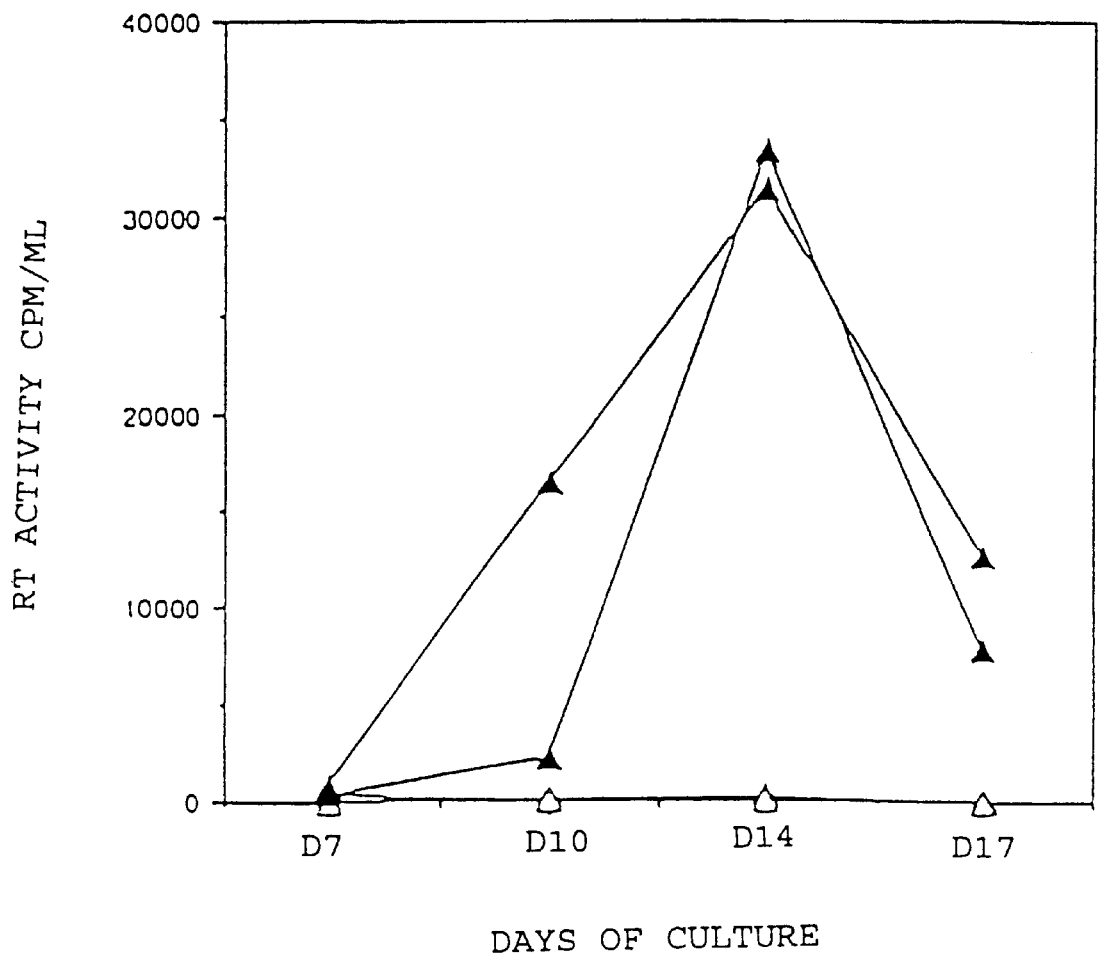

LEGEND TO FIG. 7
NEUTRALIZATION OF HIV-1 BRU-1 WITH THE SERUM OF BUB JE (1/50) ON PBL

—△— BUB JE 50
—△— BUB JE 50'
—▲— BRU
—▲— BRU'

Figure 8:
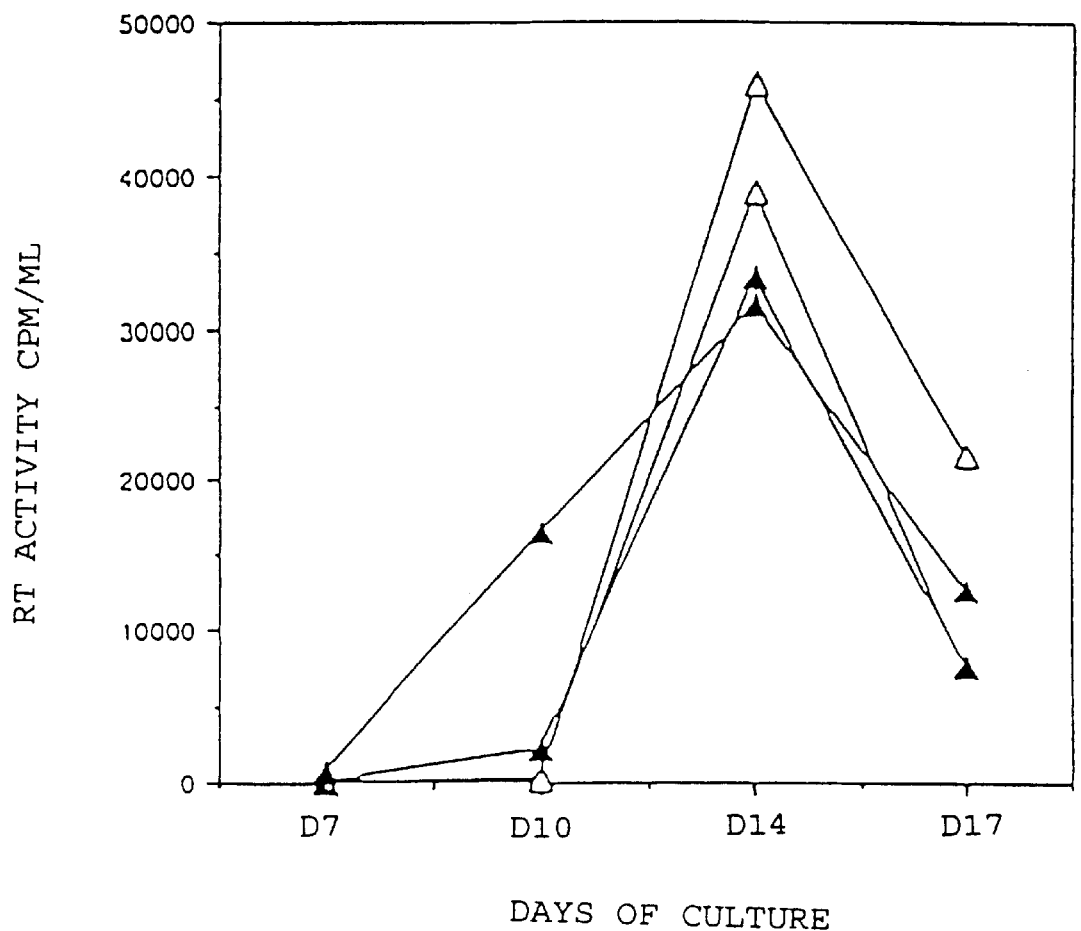

LEGEND TO FIG. 8
EFFECT OF THE SERUM SAU CH (1/50) ON THE PRODUCTION OF HIV-1 BRU-1 ON PBL

—△— SAU CH 50
—△— SAU CH 50'
—▲— BRU
—▲— BRU'

Figure 9:
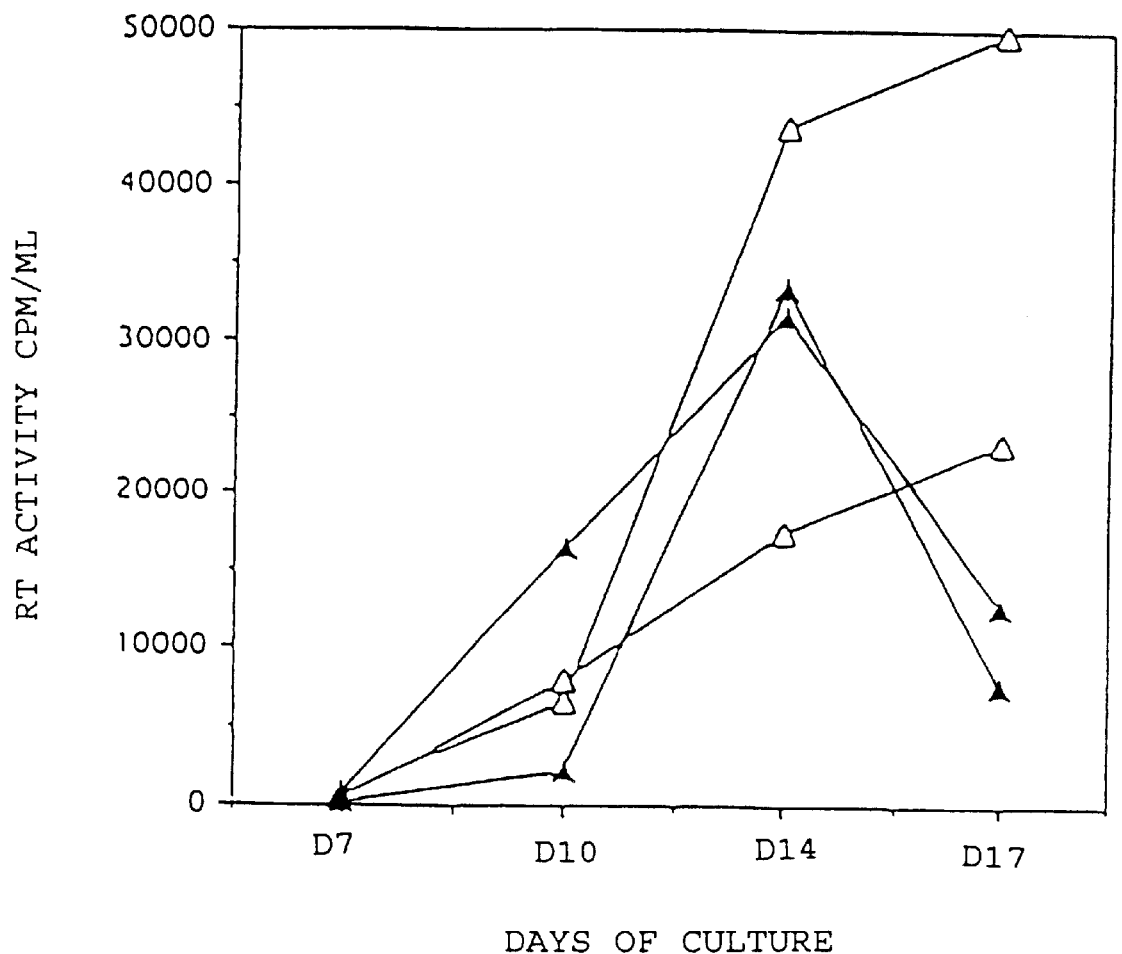

LEGEND TO FIG. 9
EFFECT OF A SERUM OF AN HIV- PATIENT ON THE PRODUCTION OF HIV-1 ON PBL

—△— SN5
—△— SN5'
—▲— BRU
—▲— BRU'

Figure 10:
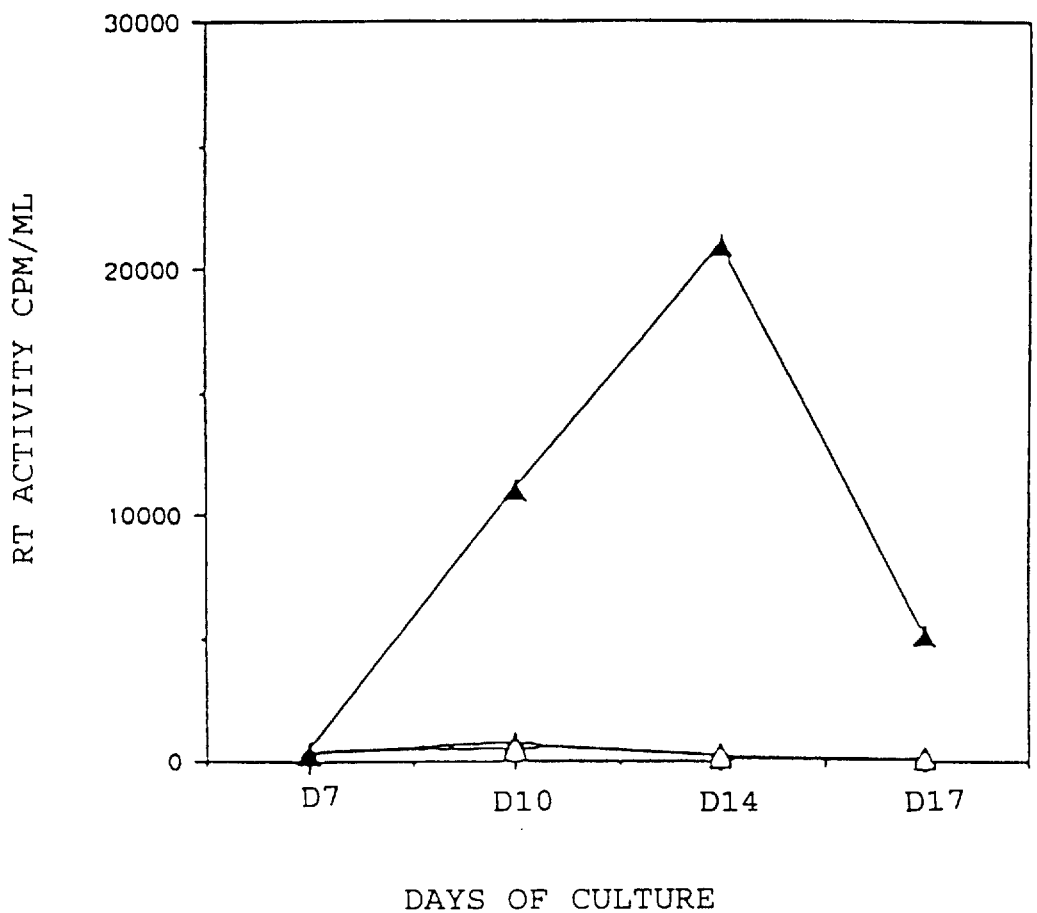

LEGEND TO FIG. 10
NEUTRALIZATION OF HIV-1 NDK WITH THE SERUM MEC EV (1/50) ON PBL

| LEGEND TO THE FIGS. | LEGEND TO THE FIGS. |
|---|---|
| —△— MEC EV 50<br>—△— MEC EV 50'<br>—▲— NDK 5-4 | —△— SAU CH 50<br>—△— SAU CH 50'<br>—▲— NDK 5-4 |

Figure 11:
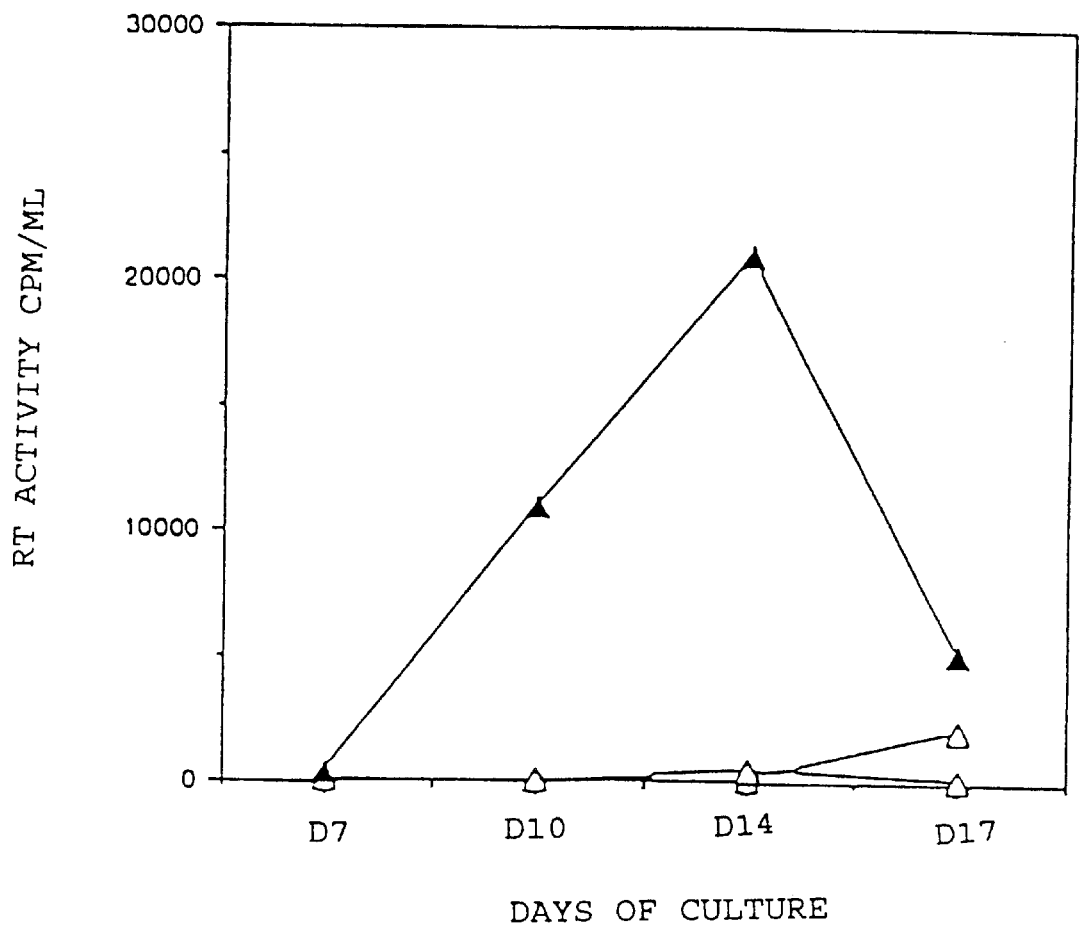

LEGEND TO FIG. 11
NEUTRALIZATION OF HIV-1 NDK WITH THE SERUM BUB JE (1/50) ON PBL

—△— BUB JE 50
—△— BUB JE 50'
—▲— NDK 5-4

Figure 12:
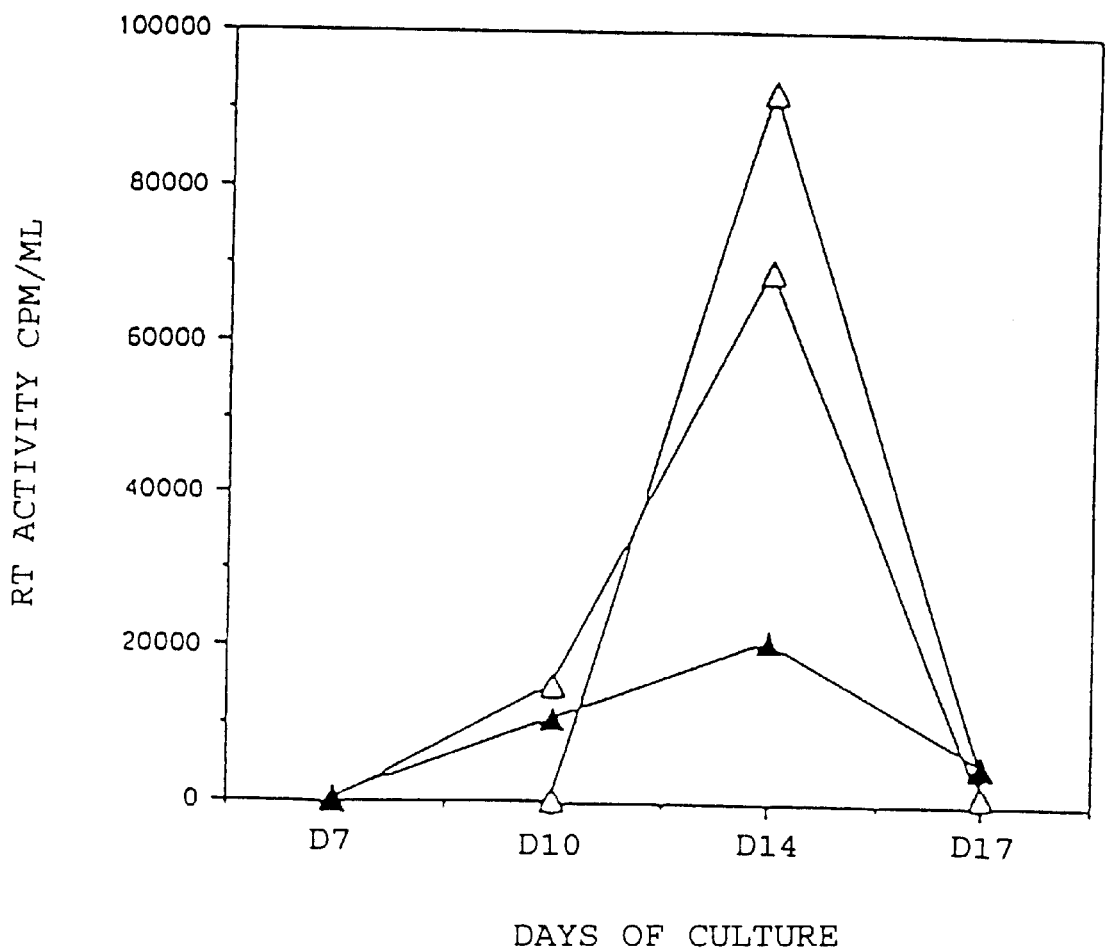

LEGEND TO FIG. 12
EFFECT OF THE SERUM SAU CH (1/50) ON THE PRODUCTION OF HIV-1 NDK ON PBL

Figure 13:
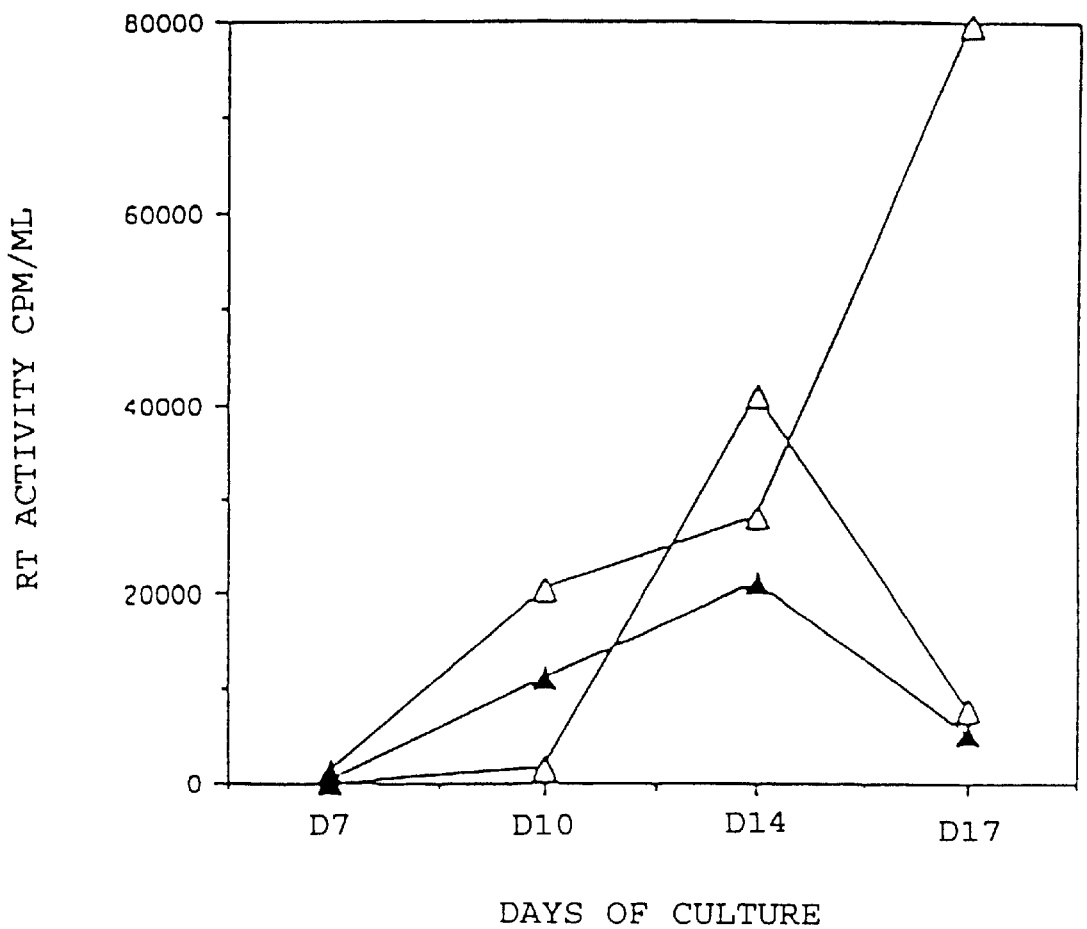

LEGEND TO FIG. 13
EFFECT OF A SERUM OF AN HIV- PATIENT ON THE PRODUCTION OF HIV-1 NDK ON PBL

—△— SN5 50
—△— SN5 50'
—▲— NDK 5-4

What is claimed is:

1. An immunogenic composition comprising at least one isolated β2-microglobulin peptide that is 15 amino acids or less and contains the amino acid sequence Pro-Lys-Ile, wherein said peptide forms a cryptic epitope.

2. An immunogenic composition comprising at least one isolated peptide selected from the group consisting of SEQ ID NOS 1–21, and SEQ ID NO 22.

3. The composition according to claim 2, wherein said peptide is bound to a carrier system.

4. The composition according to claim 3, wherein said carrier system comprises one or more protein fragments linked to the N- or C-terminal end of said peptide by a peptide bond.

5. The composition according to claim 2, wherein said carrier system is linked to said peptide by a nonpeptide bond.

6. The composition according to claim 2, wherein said peptide comprises the R7V sequence, wherein said R7V sequence comprises the amino acid sequence Arg-Thr-Pro-Lys-Ile-Gln-Val.

7. The composition according to claim 2 comprising two or more of said peptides.

8. The composition according to claim 3, wherein said carrier system is selected from the group consisting of albumins, Keyhole Limpet Hemocyanin, and Multiple Antizenic Peptide.

9. The composition according to claim 2, wherein said peptide is expressed in a host cell.

10. The composition according to claim 9, wherein said cell is a eukaryotic or plant cell.

11. The immunogenic composition according to claim 2, wherein said isolated peptide is selected from the group consisting of SEQ ID NOS 1, SEQ ID NOS 3–5, SEQ ID NOS 7–10, and SEQ ID NO 22.

12. An immunogenic composition, comprising at least one isolated β2-microglobulin cryptic epitope, wherein said epitope comprises the amino acid sequence Pro-Lys-Ile.

* * * * *

UNITED STATES PATENT AND TRADEMARK OFFICE
CERTIFICATE OF CORRECTION

PATENT NO. : 6,133,902  
DATED : September 5, 2000  
INVENTOR(S) : Jean-Claude Chermann et al.

Page 1 of 1

It is certified that error appears in the above-identified patent and that said Letters Patent is hereby corrected as shown below:

<u>Title page,</u>  
Item [73], Assignee, please change "Institut National de la Santa et de la Recherche Medicale (Inserm)" to -- Institut National de la Santé et de la Recherche Medicale (Inserm) --.

<u>Columns 19 and 20,</u>  
Table 5b, line 19, please change "BRU $10^{-3}$" to -- BRU $10^{-2}$ --.

Signed and Sealed this

Third Day of September, 2002

*Attest:*

*Attesting Officer*

JAMES E. ROGAN  
*Director of the United States Patent and Trademark Office*

```
                        SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
         (A) LENGTH: 15 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:1:

Ile Gln Arg Thr Pro Lys Ile Gln Val Tyr Ser Arg His Pro Ala
1               5                  10                  15

(2) INFORMATION FOR SEQ ID NO:2:

(i) SEQUENCE CHARACTERISTICS:
         (A) LENGTH: 15 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:2:

Phe His Pro Ser Asp Ile Glu Val Asp Leu Leu Lys Asp Gly Glu
1               5                  10                  15

(2) INFORMATION FOR SEQ ID NO:3:

(i) SEQUENCE CHARACTERISTICS:
         (A) LENGTH: 15 amino acids
         (B) TYPE: amino acid
```

(C) STRANDEDNESS:
            (D) TOPOLOGY: linear (ii) MOLECULE TYPE: peptide (xi) SEQUENCE DESCRIPTION: SEQ ID NO:3:

Ala Cys Arg Val Asn His Val Thr Leu Ser Gln Pro Lys Ile Val
1               5                  10                  15

(2) INFORMATION FOR SEQ ID NO:4:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:4:

Arg Thr Pro Lys Ile Gln Val
1               5

(2) INFORMATION FOR SEQ ID NO:5:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:5:

Ser Gln Pro Lys Ile Val Lys
1               5

(2) INFORMATION FOR SEQ ID NO:6:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:6:

Phe His Pro Ser Asp Ile Glu
1               5

(2) INFORMATION FOR SEQ ID NO:7:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Thr Leu Ser Arg Thr Pro Lys Ile Gln Val
1               5                  10

(2) INFORMATION FOR SEQ ID NO:8:

(i) SEQUENCE CHARACTERISTICS:
            (A) LENGTH: 10 amino acids

```
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Ile Tyr Leu Thr Gln Arg Lys Ile Lys Val
1               5                  10

(2) INFORMATION FOR SEQ ID NO:9:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Ile Gln Arg Thr Pro Lys Ile Gln Val Tyr
1               5                  10

(2) INFORMATION FOR SEQ ID NO:10:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:10:

Thr Leu Ser Gln Pro Lys Ile Val Lys Asn
1               5                  10

(2) INFORMATION FOR SEQ ID NO:11:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:11:

Ile Gln Arg Thr Pro Gln Ile Val Lys Trp
1               5                  10

(2) INFORMATION FOR SEQ ID NO:12:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:12:

Ile Gln Arg Thr Pro Asn Ile Val Lys Trp
1               5                  10

(2) INFORMATION FOR SEQ ID NO:13:

(i) SEQUENCE CHARACTERISTICS:
```

(A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Cys Tyr Asn Pro Ser Asp Ile Glu
1               5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Tyr Cys Asn Pro Glu Ser Thr
1               5

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

Asn Phe Leu Asn Cys Tyr Val Ser
1               5

(2) INFORMATION FOR SEQ ID NO:16:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

Leu Asn Cys Tyr Val Ser Pro Ser Asp
1               5

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

Lys Thr Pro Gln Ile Gln Val
1               5

(2) INFORMATION FOR SEQ ID NO:18:

```
        (i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:18:

Phe His Pro Pro Gln Ile Glu
1               5

(2) INFORMATION FOR SEQ ID NO:19:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:19:

Phe His Pro Pro His Ile Glu
1               5

(2) INFORMATION FOR SEQ ID NO:20:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:20:

Ala Glu Pro Lys Thr Val Tyr
1               5

(2) INFORMATION FOR SEQ ID NO:21:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:21:

Ser Gln Pro Lys Thr Val Tyr
1               5

(2) INFORMATION FOR SEQ ID NO:22:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:22:

Ile Leu Ser Arg Thr Pro Lys Ile Gln Val
1               5                   10

(2) INFORMATION FOR SEQ ID NO:23:
```

(i) SEQUENCE CHARACTERISTICS:
           (A) LENGTH: 9 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:23:

Arg Thr Pro Lys Ile Gln Val Gly Tyr
1               5

(2) INFORMATION FOR SEQ ID NO:24:

(i) SEQUENCE CHARACTERISTICS:
           (A) LENGTH: 20 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:24:

Asn Asn Asn Thr Arg Lys Ser Ile Arg Ile Gln Arg Gly Pro Gly Arg
1               5                  10                  15

Ala Phe Val Thr
            20

(2) INFORMATION FOR SEQ ID NO:25:

(i) SEQUENCE CHARACTERISTICS:
           (A) LENGTH: 34 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(xi) SEQUENCE DESCRIPTION: SEQ ID NO:25:

ACACCAAAGA TACAAGTTGT TACAAATAGG AAAA                                34

(2) INFORMATION FOR SEQ ID NO:26:

(i) SEQUENCE CHARACTERISTICS:
           (A) LENGTH: 35 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(xi) SEQUENCE DESCRIPTION: SEQ ID NO:26:

TTGTATCTTT GGTGTTCTCT GGATCCGGAT ACTTT                               35

(2) INFORMATION FOR SEQ ID NO:27:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(xi) SEQUENCE DESCRIPTION: SEQ ID NO:27:

```
                                          -continued

CGTACACCAA AAATCCAGGT CCAGAGAGGA CCA                                        33

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:28:

GATTTTTGGT GTACGCGTAT TGTTGTTGGG TCT                                        33
```